United States Patent
Nachaliel et al.

(10) Patent No.: US 6,560,480 B1
(45) Date of Patent: *May 6, 2003

(54) LOCALIZATION OF ANOMALIES IN TISSUE AND GUIDANCE OF INVASIVE TOOLS BASED ON IMPEDANCE IMAGING

(75) Inventors: Ehud Nachaliel, Lower Galilee (IL); Amos Ori, Lower Galilee (IL); Abraham Saad, Haifa (IL); Andrew L. Pearlman, Shorashim (IL)

(73) Assignee: TransScan Medical Ltd., Migdal-Haemek (IL)

(*) Notice: Subject to any disclaimer, the term of this patent is extended or adjusted under 35 U.S.C. 154(b) by 0 days.

This patent is subject to a terminal disclaimer.

(21) Appl. No.: 09/460,699

(22) Filed: Dec. 14, 1999

Related U.S. Application Data

(63) Continuation-in-part of application No. 09/150,224, filed on Sep. 9, 1998, now Pat. No. 6,055,456, which is a continuation of application No. 08/725,927, filed on Oct. 4, 1996, now Pat. No. 5,810,742, which is a continuation-in-part of application No. PCT/US95/06141, filed on May 19, 1995.

(30) Foreign Application Priority Data

| Oct. 24, 1994 | (IL) | 111381 |
| Apr. 20, 1995 | (IL) | 113454 |
| Oct. 5, 1995 | (IL) | 115525 |

(51) Int. Cl.[7] .............................................. A61B 5/05
(52) U.S. Cl. ....................................................... 600/547
(58) Field of Search ................................. 600/372, 382, 600/384, 386, 461, 476, 477, 478, 547; 601/21; 324/600, 601, 609, 611; 378/70

(56) References Cited

U.S. PATENT DOCUMENTS

| 4,082,087 A | 4/1978 | Howson |
| 4,291,708 A | 9/1981 | Frei et al. |
| 4,387,721 A | 6/1983 | Enjoji |
| 4,458,694 A | 7/1984 | Sollish et al. |
| 4,493,039 A | 1/1985 | Gregory |

(List continued on next page.)

FOREIGN PATENT DOCUMENTS

| DE | 42 25 112 C1 | 12/1993 |
| EP | 0 000 759 A | 2/1979 |
| EP | 0 050 353 A | 10/1981 |
| EP | 0 190 043 A | 8/1986 |
| FR | 2 655 835 A1 | 6/1991 |

(List continued on next page.)

OTHER PUBLICATIONS

Riu, P. et al.; "A Broadband System for Multifrequency Static Imaging in Electrical Impedance Tomography"; Clin. Physiol. Meás.; 1992; vol. 13; Suppl. A; pp. 61–65.

Masuda et al.; "Topographical Map of Innervation Zones within Single Motor Units Measured with a Grid Surface Electrode"; IEEE Transactions on Biomedical Engineering; vol. 35; No. 8; Aug. 1988 (1988–08); pp. 823–628; XP000005699.

(List continued on next page.)

Primary Examiner—George Manuel
(74) Attorney, Agent, or Firm—Carella Byrne Bain Gilfillan Cecchi et al.; Elliot M. Olstein; William Squire

(57) ABSTRACT

A method of impedance imaging of a region within a body. The method includes positioning a multi-element probe, including a plurality of sensing elements, on one side of the region, positioning a plurality of electrifying elements on a second side of the region, electrifying the plurality of electrifying elements, measuring a signal at at least some of the sensing elements of the multi-element probe, and analyzing the region responsive to the measured signals and the positions of the electrifying elements.

131 Claims, 10 Drawing Sheets

U.S. PATENT DOCUMENTS

| | | | |
|---|---|---|---|
| 4,510,939 A | * 4/1985 | Brenman et al. | 600/384 |
| 4,537,203 A | 8/1985 | Machida | |
| 4,539,640 A | 9/1985 | Fry et al. | |
| 4,617,939 A | 10/1986 | Brown et al. | |
| 4,763,660 A | 8/1988 | Kroll et al. | |
| 4,805,621 A | 2/1989 | Heinze et al. | |
| 4,819,658 A | 4/1989 | Kolodner | |
| 4,823,797 A | 4/1989 | Heinze et al. | |
| 4,896,673 A | 1/1990 | Rose et al. | |
| 5,045,249 A | 9/1991 | Jin et al. | |
| 5,063,937 A | 11/1991 | Ezenwa et al. | |
| 5,070,862 A | * 12/1991 | Berlant | 601/21 |
| 5,099,846 A | 3/1992 | Hardy | |
| 5,143,079 A | 9/1992 | Frei et al. | |
| 5,178,147 A | 1/1993 | Ophir et al. | |
| 5,247,938 A | 9/1993 | Silverstein et al. | |
| 5,272,624 A | 12/1993 | Gisser et al. | |
| 5,280,429 A | * 1/1994 | Withers | 378/70 |
| 5,282,840 A | 2/1994 | Hudrlik | |
| 5,295,483 A | 3/1994 | Nowacki et al. | |
| 5,353,802 A | 10/1994 | Ollmar | |
| 5,454,377 A | 10/1995 | Dzwonczyk et al. | |
| 5,626,146 A | * 5/1997 | Barber et al. | 600/547 |
| 5,810,742 A | 9/1998 | Pearlman | |
| 6,122,544 A | * 9/2000 | Organ | 600/547 |

FOREIGN PATENT DOCUMENTS

| | | |
|---|---|---|
| GB | 2 138 148 A | 10/1984 |
| GB | 2 273 987 | 7/1994 |
| GB | 2 276 326 A | 9/1994 |
| WO | WO 91/13584 A | 9/1991 |
| WO | WO 93/23112 | 11/1993 |
| WO | WO 94/20012 A | 9/1994 |
| WO | WO 96/12439 | 5/1996 |
| WO | WO 99/48422 | 9/1999 |

OTHER PUBLICATIONS

Monster et al.; "A System for the Rapid Acquisition of Surface Potential Maps of Human Skeletal Muscle Motor Units"; IEEE Transactions on Biomedical Engineering; vol. 27; No. 2; Feb. 1980 (1980–02); pp. 110–112; XP002114215.

Riu et al.; "In Vivo Static Imaging for the Reactive Parts in Electrical Impedance Tomography Using Multifrequency Techniques"; Proceedings on the Annual International Conference of the Engineering in Medicine and Biology Society; vol. 5; No. 14; Oct. 1992 (1992–10); pp. 1706–1707; XP000514393.

Cespedes et al.; "Elastrography: Elastic Imaging Using Ultrasound with Application to Muscle and Breast In Vivo"; Ultrasound Imaging; vol. 15, No. 2; Apr. 1993 (1993–04); pp. 73–78; XP000383142.

Eyuboglu et al.; "In Vivo Imaging of Cardiac Related Impedance Changes"; IEEE Engineering in Medicines and Biology vol. 8, No. 1; Mar. 1989 (1989–03); pp. 39–45; XP000002279.

Record et al.; "Multifrequency Electrical Impedance Tomography"; Clinical Physics and Physiological Measurement; Supplement A; vol. 13; Jul. 1992 (1992–07); pp. 47–50; XP000431598.

Huang, Z. et al.; "Bioimpedance Measurement: Theory, Experiment and Application"; Proceedings of the Ninth Annual Conference of the IEEE Engineering in Medicine and Biology Society; vol. 3; Nov. 1987 (1987–11); pp. 1416–1427; XP000015434.

Israeli Office Action.

Man et al., "Results of Pre–Clinical Test for Breast Cancer Detection by Dielectric Measurements", International Conference of Medical and Biological Engineering, V International Conference of Medical Physics, 30.4, Jerusalem, Israel, Aug. 12–24, 1979.

International Search Report.

Internation Preliminary Examination Report.

Written Opinion.

G. Piperno et al., "Breast Cancer Screening by Impedance Measurements", Frontiers Med. Biol., vol. 2, 1990, pp. 111–117 plus two attached pages "Mammoscan: A Promising New Technology for Breast Screening and Diagnosis" and "Mammoscan Breast Impedance System".

Estelle et al., "Capacitive Sensors for In–Vivo Measurements of the Dielectric Properties of Biological–Materials", IEEE Trans. Inst & Meas., vol. 37, No. 1, Mar. 1988, pp. 101–105.

E. Gersing, "Messung der elecktrischen Impedance von Organen–Apparative Ausrustung fur forschung und klinishe Anwendung", Bimed. Technik 36 (1991), pp. 6–11 (including abstract in english).

J. Vrana et al., "Mesure de L"Impedance des Tissus Hepatiqueles pas des Processus Lesionel Ann. Gastroentresol. Hepatol., 1992, 28, No. 4, pp. 165–168 (including abstract in english).

V. Rajshekhar, "Continuous Impedance Monitoring During CT–Guided Stereotactic Surgery: Relative Value Cystic and Solid Lesions", British journal of Neurosurgery (1992), pp. 439–444.

J.J. Mastrototaro et al. "Rigid and Flexible Thin–Film Multi–Electrode Arrays for Transmural Cardiac Recording" IEEE Trans. Biomed. Engr., vol. 39, No. 3, Mar. 1992, pp. 271–279.

D.S. Buckles et al., "Image–Base Display of Activation Patterns Derived from Scattered Electrodes", I Trans. Biomed. Engr., vol. 42, No. 1, Jan. 1995, pp. 111–115.

G.A. Urban et al., Development of a Multiple Thin–Film Semimicro DC–Probe for Intracerebral Recording IEEE Trans. Biomed. Eng., vol. 37, No. 10, Oct. 1990, pp. 913–917.

R.W.M. Smith et al., "A Real–Time Electrical Impedance Tomography System for Clinical Use–Design and Preliminary Results", IEEE Trans. Biomed. Eng., vol. 42, Feb. 1995, pp. 133–139.

A.J. Surowiec et al., Dielectric Properties of Breast Carcinoma and the Surrounding Tissues:, IEEE Trans. Biomed. Eng., vol. 35, No. 4, Apr. 1988, pp. 257–263.

M. Heimbach "Measures of Performance", Electrical Impedance Tomography, (12.1), 1990, pp. 158–174.

R.J. Davies et al., "Detection of the Cancer–Prone Colon, using Transepothelial Impedance Analysis", Arhc Surg., vol. 124, Apr. 1989, pp. 480–484.

T. Morimoto et al., "A Study of the Electrical Bio–Impedance of Tumors", Journal of Investigative Surgery, vol. 6, 1993, pp. 25–32.

Anah, J. et al.; "Multi–Function Interface Unit for Applied Potential Tomography;"1988; Proceedings of the Annual InternationalConference of the IEEE Engineeringin Medicine and Biology Society (IEEE Cat. No. 88CH2566–8), New Orleans; Nov. 4–7, 1988; pp. 287–288; vol. 1; XP002171794.

Kotre, C.J.; "Subsurface Electrical Impedance Imaging Using Orthogonal Linear Electrode Arrays;" Jan. 16, 1996; IEE Proceedings:Science, Measurementand Technology; IEE; vol. 143, No. 1; pp. 41–46; XP006006750.

Rigaud, B. et al.; "Experimental Acquisition System for Impedance Tomography with Active Electrode Approach;" Nov. 1, 1993; Medical and Biological Engineering and Computing; Great Britain; Peter Peregrinus Ltd.; Stevenage; vol. 31, No. 6; pp. 593–599; XP000415771.

* cited by examiner

LOCALIZATION OF ANOMALIES IN TISSUE AND GUIDANCE OF INVASIVE TOOLS BASED ON IMPEDANCE IMAGING

This application is a continuation-in-part of U.S. patent application Ser. No. 09/150,224 filed Sep. 9, 1998 now U.S. Pat. No. 6,055,456 which is a continuation of U.S. patent application Ser. No. 08/725,927 filed Oct. 4, 1996, now U.S. Pat. No. 5,810,742, which is a continuation-in-part of PCT application PCT/US95/06141 which was filed on May 19, 1995, and was published on May 2, 1996 as WO96/12439, the disclosures of all of which are incorporated herein by reference in their entirety.

FIELD OF THE INVENTION

The present invention relates to systems for tissue characterization based on impedance measurements, and in particular to systems for determining the locations of anomalies based on impedance measurements.

BACKGROUND OF THE INVENTION

Variations in electrical impedance of the human tissue may be indicative of tumors, lesions and other anomalies. For example, U.S. Pat. No. 4,291,708 to Frei, and U.S. Pat. No. 4,458,694, and the article, "Breast Cancer Screening by Impedance Measurements," by G. Piperno et al., Frontiers Med. Biol. Eng., Vol. 2 pp. 111–117, the disclosures of which are incorporated herein by reference, describe systems for determining the impedance between a point on the surface of the skin and some reference point on the body of the patient. With the use of a multi-element probe, a two-dimensional impedance map of an organ such as a breast can be generated. The impedance map, describing variations in impedance along the tissue of the organ, can be used for the detection of tumors and especially malignant tumors.

An exemplary system for tissue characterization includes a multi-element probe which is pressed against the skin of a patient. The elements of the multi-element probe are kept at a ground voltage and an electrification signal is applied at some point on the patient. The elements of the multi-element probe serve as sensors which measure the current incident on the sensors and accordingly determine a measure of the impedance of the tissue beneath each element of the probe. Using the impedance values determined by the elements, a two-dimensional impedance map is generated, which map is used to detect abnormal tissue.

It is understood, however, that the system indicates the locations of abnormal tissue as a function of the locations on the skin, and gives little indication of the depth of the abnormal tissue beneath the skin. In addition, the ability to find a tumor of abnormal tissue decreases with the distance of the tumor from the surface to which the probe is pressed.

U.S. Pat. Nos. 4,617,939 and 4,539,640 describe three-dimensional mapping of the tissue impedance of the body. These patents describe measuring the impedance on a plurality of surfaces surrounding an organ and producing a three-dimensional map based on Poison's equation.

However, in many organs it is not feasible to place a sufficient number of probes on surfaces of the organ to receive a satisfactory impedance image. In addition, in some cases it is desired that the point from which the electrification signal is applied be as close as possible to the examined organ and/or that the signal be applied along a large surface. Furthermore, in some cases the image is required during a surgical procedure, especially during minimal invasive procedures, such as biopsy taking using a biopsy needle. In such cases, a surgeon performing the procedure needs to have access to the surface of the organ.

Even when there are sufficient vacant surfaces on the organ, three-dimensional mapping is cumbersome and requires complex algorithms in order to solve Poison's equation. These complex algorithms introduce errors into the measurements and/or magnify measurement errors. In addition, when the organ includes a plurality of anomalies, separation between the different anomalies becomes very difficult, since all the anomalies influence the measurements on all the surfaces.

U.S. Pat. No. 5,353,802 to Ollmar, the disclosure of which is incorporated herein by reference, describes a device for depth selective detection and characterization of surface phenomena based on impedance measurements. The device includes an electrode for applying electrical signals, an electrode for measuring signals and a control electrode for controlling the depth of the applied signals.

SUMMARY OF THE INVENTION

An object of some preferred embodiments of the present invention is to provide methods and apparatus for determining the depth of an anomaly within an organ of a patient, relative to a probe placed on a surface of the organ. The depth is determined using signals detected by the probe on the surface.

It is an object of some preferred embodiments of the present invention to provide methods for detecting anomalies which are deep within an organ, i.e., far from a probe of sensors used to detect the anomaly, which anomalies are not detectable using methods known in the art.

It is an object of some preferred embodiments of the present invention to provide a method for determining the depth of an anomaly within an organ, which method does not depend on the shape of the anomaly.

It is an object of some preferred embodiments of the present invention to provide improved methods for directing an invasive tool, such as a biopsy needle, toward an anomaly.

It is an object of some preferred embodiments of the present invention to provide improved methods for determining contact between an invasive tool and an anomaly.

An aspect of some preferred embodiments of the present invention relates to applying electrifying signals for impedance imaging of a body part at specific points relative to an array of sensors used to sense the effect of the signals. The position of an anomaly (e.g., lesion, tumor, cyst) is preferably determined according to at least one surface map generated by the array of sensors in relation to the positions of the specific points from which the electrifying signals are applied. In some preferred embodiments of the invention, the electrifying signals are applied to a small region relative to the area of the array of sensors.

In some preferred embodiments of the present invention, the electrifying signals are applied in a specific spatial pattern which increases the signal to noise ratio in the array of sensors of signals originating from anomalies which are to be detected. In a preferred embodiment in which the signals are applied from a surface opposite the sensors, the dimensionality of the applied signals is reduced so that deep anomalies receive stronger signals than anomalies close to the sensors. For example, instead of applying signals from an entire surface, signals are applied along a line, from a single point, or in the form of a dipole.

Preferably, the electrifying signals are applied in lines which are long and narrow relative to the size of an average anomaly. Alternatively or additionally, the electrifying signals are applied in other patterns and sizes, such as, large and small rings, circles, squares and rectangles. Further alternatively or additionally, electrifying signals are applied in a few geometrically unconnected regions.

In some preferred embodiments of the present invention, the electrifying signals are applied in a form which includes signals with different phases in a predetermined spatial relationship, e.g., with substantially opposite polarities. Preferably, the applied signals are in the form of a dipole. In a preferred embodiment, the electrifying signals are in the form of two parallel straight lines which have opposite and equal polarities. The distance between the lines forming the dipole is preferably adjustable.

An aspect of some preferred embodiments of the present invention relates to determining the depth of an anomaly within an organ. In a preferred embodiment of the invention, the depth is determined by inducing an electrical dipole of known orientation within the anomaly. The dipole within the anomaly induces a dipole field within the organ and this field influences the sensed values of the multi-element probe. When the dipole within the anomaly causes a field perpendicular to the probe it induces a peak within the sensors. The location and strength of the peak are indicative of the location of the anomaly. When the direction of the field of the dipole within the anomaly is parallel to the multi-element probe, the dipole induces two peaks within the sensors and the distance between the peaks is indicative of the depth of the anomaly within the organ.

The position of an anomaly, including its depth, is preferably determined based on a plurality of impedance maps. Preferably, the plurality of impedance maps are generated responsive to respective electrifying patterns which are applied in a manner systematically covering a surface of the imaged body part.

In a preferred embodiment of the present invention, the body part, which is for example a breast, is pressed between a pair of multi-element probes. Preferably, one of the probes serves as an electrifying probe which provides electrifying signals to the breast and the other probe serves as the array of sensors. The patterns of electrifying signals are preferably provided by activating specific elements or groups of elements of the electrifying probe.

An aspect of some preferred embodiments of the present invention relates to a method of sensing the electric field in impedance imaging while the influence of the sensors on the field is minimized. In a preferred embodiment of the present invention, the array of sensors senses voltages using sensors with a high input impedance.

In some preferred embodiments of the present invention, the electrifying signals are sensed at any single time only by a sub-group of the sensors on the probe. Preferably, a single map covering substantially all the sensors of the probe is generated in a plurality of steps, each step including sensing from a different sub-group of the sensors. Preferably, those sensors not presently used in generating the map are kept floating so that they do not affect the currents in the body part. In a preferred embodiment, only a small percentage of the sensors of the sensing array are active when readings are taken by the sensor array. Preferably, the array of sensors comprises low impedance sensors which measure currents and most of the sensors are kept floating when a reading is taken. Therefore, the sensors do not force the currents to be perpendicular to the sensors and only nominally affect the electric fields in the organ.

In a preferred embodiment, in each step a subset of sensors which are used in producing the map are chosen according to the location, size, frequency and/or any other attribute of the electrifying signals. Alternatively, the subsets for each step are chosen so as to sequentially cover the entire area of the probe.

An aspect of some preferred embodiments of the present invention relates to normalizing the generated map so as to remove an uneven direct effect of the electrifying signals on the map. Preferably, a normalizing value is subtracted from each area which receives equal direct effect from the electrifying signals. For example, when the electrifying signals are applied along straight lines the normalizing values are calculated for each line. Preferably, the normalizing values are calculated as the average of all the sensed values in the area from which the normalized value is subtracted.

An aspect of some preferred embodiments of the present invention relates to generating electrifying signals for impedance imaging from an invasive tool within an organ being imaged. In a preferred embodiment of the present invention, one or more sensing probes pressed against a surface detect the signals from the invasive tool, as the tool is moved toward an anomaly. As the invasive tool approaches the anomaly, the effect of the anomaly on the charge induced within the anomaly and thus on signals sensed by the sensing probe is enhanced. Thus, the image formed by the sensing probe can be used to monitor, manually or automatically, the movements of the probe toward the anomaly. When the invasive tool touches or enters the anomaly, the direct electrification of the anomaly by the tool induces a detectable change in the signals detected due to the anomaly.

In preferred embodiments of this aspect, an additional surface probe is used to apply a signal with opposite polarity from the signal from the invasive tool. Thus, a dipole is induced within the anomaly, allowing easier detection of the signals from the anomaly. When the invasive tool is very close to (or touches) the anomaly the polarity of the dipole in the anomaly changes, providing additional indication of the proximity of the tool to the anomaly.

In a preferred embodiment of the present invention, the phases of the applied signals from the surface probe with respect to those of the invasive tool are changed during the insertion in order to induce additional detectable changes in the dipole of the anomaly.

An aspect of some preferred embodiments of the present invention relates to determining the orientation of an invasive tool within an organ. Preferably, a single electric voltage level is applied to the invasive tool over an entire length which is being tracked. The width of the tool in the surface map is indicative of the depth of the tool. The orientation of the tool is preferably determined from the difference in the width of the tool in the surface map along the length of the tool and its orientation on the surface map.

In a preferred embodiment of the present invention, external probes are used to induce a monotonously changing-with-position electric field within the organ. When an electric voltage is applied to the needle within the region, the needle appears brighter than its surroundings in those areas in which the needle has a higher voltage than its surroundings. On the other hand, in areas in which the needle is at a lower voltage than its surroundings the needle appears darker than its surroundings. In a preferred embodiment, the voltage applied to the needle is varied until the needle appears most clearly relative to the surroundings and/or until the depth and/or orientation of the needle are most easily determined.

There is therefore provided in accordance with a preferred embodiment of the present invention, a method of impedance imaging of a region within a body, including positioning a multi-element probe, including a plurality of sensing elements, on one side of the region, positioning a plurality of electrifyable elements on a second side of the region, electrifying at least one of the plurality of electrifyable elements, measuring a signal at at least some of the elements of the multi-element probe, and analyzing the region responsive to the measured signals and the positions of the electrifyable elements.

Preferably, the electrified elements cover an area which is less than ten percent of the face area of the multi-element probe. Preferably, positioning the electrifyable elements includes mounting the electrifyable elements on an invasive tool inserted into the region. Preferably, electrifying the electrifyable elements includes applying at least two electrifying signals with different phases. Preferably, applying the at least two electrified signals includes applying signals of substantially opposite polarity.

Preferably, positioning the multi-element probe includes holding substantially all of the sensing elements of the multi-element probe at a same potential. Alternatively or additionally, positioning the multi-element probe includes positioning a probe of which a plurality of the sensing elements are simultaneously connected to respective sensors and measuring the signal at at least some of the elements includes measuring at less than all the plurality of sensing elements which are simultaneously connected.

Preferably, measuring includes measuring using less than ten percent of the sensing elements at any single time. Preferably, at least some of the sensing elements have a low input impedance. Alternatively or additionally, at least some of the sensing elements have a high input impedance. Preferably, positioning the electrifyable elements on the second side of the region includes positioning the elements on a side of the region substantially opposite the multi-element probe. Preferably, analyzing the region includes producing an impedance map responsive to the measured signals. Preferably, producing the impedance map includes normalizing the impedance map responsive to the positions of the electrified elements.

Preferably, normalizing the impedance map includes subtracting a predetermined background map from the produced map. Alternatively or additionally, normalizing the impedance map includes subtracting from values of the measured signals of at least one group of elements a representative value which is a function of the measured values of the group. Preferably, the representative value of the group includes an average or minimum of the measured values of the group.

Preferably, the electrified elements form a long and narrow straight line of elements. Preferably, analyzing the region includes determining whether a suspected lesion exists in the region. Alternatively or additionally, analyzing the region includes determining a location of a lesion within the region. Preferably, determining the location of the lesion includes determining the depth of the lesion below the multi-element probe. Preferably, determining the depth of the lesion includes generating a map of sensed signals responsive to the signals measured by the at least some sensing elements of the multi-element probe and determining the depth responsive to a distance between peaks in the generated map.

Preferably, positioning the electrifyable elements includes positioning a second multi-element probe including the electrifyable elements. Preferably, the method includes sequentially electrifying and measuring while electrifying different sub-groups of elements of the second multi-element probe. Preferably, sequentially electrifying includes sequentially electrifying columns of the second multi-element probe. Alternatively or additionally, sequentially electrifying includes sequentially electrifying pairs of one-dimensional strips of the second multi-element probe. Preferably, electrifying the pairs of one-dimensional strips includes electrifying the one-dimensional strips with signals of respective opposite polarities. Preferably, electrifying the pairs of one-dimensional strips includes electrifying pairs of one-dimensional strips which are separated by a predetermined distance, to form a dipole source of electrification.

There is further provided in accordance with a preferred embodiment of the present invention, a method of impedance imaging of a region, including positioning a multi-element probe, including a plurality of sensing elements, on one side of the region, providing electrifying signals to the region from one or more first locations, measuring a signal at at least some of the elements of the multi-element probe responsive to the signals from the one or more first locations, providing electrifying signals to the region from one or more second locations different from the first locations, and measuring a signal at at least some of the elements of the multi-element probe responsive to the signals from the one or more second locations.

Preferably, providing the electrifying signals from the first and second locations includes providing electrifying signals from a second multi-element probe. Preferably, measuring the signal at at least some of the elements includes measuring at substantially all the elements of the multi-element probe. Preferably, the method includes analyzing the region responsive to the measurements responsive to the first and second signals.

There is further provided in accordance with a preferred embodiment of the present invention, a method of impedance imaging of a region, including positioning a multi-element probe, including a plurality of sensing elements, on a surface of the region, providing an electrifying field to the region substantially in the form of a dipole, and measuring a signal at at least some of the elements of the multi-element probe responsive to the electrifying field.

Preferably, providing the dipole electrifying field includes providing signals of opposite polarity from spaced electrifyable elements. Preferably, providing the electrifying field includes providing the field from a dipole formed of parallel lines.

There is further provided in accordance with a preferred embodiment method of impedance imaging of a region, including positioning a multi-element probe, including a plurality of sensing elements, on a surface of the region, providing a plurality of electrifying fields of different phases to the region, and measuring a signal at at least some of the elements of the multi-element probe responsive to the electrifying fields.

Preferably, providing the plurality of electrifying fields includes providing fields which comprise a dipole field. Preferably, providing the plurality of electrifying signals includes providing signals which have voltages such that the sum of the voltages is substantially zero at substantially any time.

There is further provided in accordance with a preferred embodiment of the present invention, a method of impedance imaging of a region, including positioning a multi-element probe, including a plurality of sensing elements, on a surface of the region, applying an electrical field to the region, connecting at least some of the sensing elements of the multi-element probe to a sensor through a high input impedance, and measuring an electrical signal produced by at least some of the sensing elements with the high input impedance sensor.

Preferably, applying the electrical field includes applying signals to a pair of electrodes on substantially opposite sides of the region. Alternatively or additionally, applying the electrical signals to the pair of electrodes includes applying signals to a pair of electrodes positioned such that a straight line connecting the electrodes is substantially parallel to the multi-element probe.

Alternatively or additionally, applying the electrical signals to the pair of electrodes includes applying signals from a pair of electrodes positioned substantially perpendicular to the multi-element probe.

Further alternatively or additionally, applying the electrical signals from the pair of electrodes comprises applying signals from a pair of electrodes such that the combined field produced by electrification of the pair of electrodes is substantially parallel to the multi-element probe.

Preferably, applying the electrical signals includes applying signals of a different amplitude to each of the electrodes. Preferably, applying the electrical signals to the pair of electrodes includes holding one of the electrodes at a ground potential.

There is further provided in accordance with a preferred embodiment of the present invention, a method of impedance imaging of a region, including positioning a multi-element probe, including a plurality of sensing elements, on a surface of the region, positioning a pair of electrodes on substantially opposite sides of the region, electrifying the pair of electrodes to provide an electrical field between the pair of electrodes, and measuring an electrical signal by at least some of the sensing elements responsive to the electrifying of the at least one electrode.

There is further provided in accordance with a preferred embodiment of the present invention, a method of determining the position of an anomaly within a region of a body, including applying electrifying signals to the region, determining an response map along a surface of the region responsive to the applied signals, determining a point on the surface which is above the anomaly responsive to the response map, and calculating the depth from the determined point to the anomaly responsive to the response map.

Preferably, determining the response map includes determining a map which covers less than half the total surface area of the region. Preferably, determining the response map includes determining a plurality of maps generated responsive to different patterns of electrifying signals. Preferably, determining the point above the anomaly includes finding a point located between a pair of peaks on the map.

Preferably, calculating the distance includes determining a distance between the pair of peaks. Preferably, applying electrifying signals to the region includes inducing a dipole which is substantially parallel to the surface along which the response map is determined.

There is further provided in accordance with a preferred embodiment of the present invention, a method of guiding an elongate object within a region of a subject, including providing electrifying signals from at least a part of the elongate object within the region, measuring electrical signals on a surface of the region, moving the elongate object, comparing the electrical signals measured on the surface of the region before and after the movement, and determining desired movements of the object responsive to the comparison.

Preferably, the elongate object includes a biopsy needle. Preferably, providing the electrifying signals includes providing the signals from a probe mounted on the elongate object. Alternatively, providing the electrifying signals includes electrifying the elongate object. Preferably, determining the desired movements includes determining a movement direction which enhances the measured signals.

Preferably, the method includes providing electrifying signals from a surface of the region. Preferably, providing the electrifying signals from the surface includes providing signals different from the signals provided from the elongate object. Preferably, providing the electrifying signals from the surface includes providing signals of opposite polarity of the signals provided from the elongate object.

There is further provided in accordance with a preferred embodiment of the present invention, a method for determining the location of an elongate object in a region of a subject, including providing electrifying signals from at least a part of the elongate object within the region, measuring electrical signals on a surface of the region, and determining the location of the object responsive to the measured electrical signals.

Preferably, determining the desired movements includes determining when the object is touching an anomaly. Preferably, determining when the object is touching the anomaly includes determining reversal of the polarity of the measured signals.

Preferably, providing the electrifying signals includes electrifying the elongate object. Preferably, determining the location of the object includes determining the depth of a plurality of points along the object. Preferably, measuring the electrical signals includes producing a two dimensional map of signals incident on the surface of the region. Preferably, determining the location of the object includes determining the depth of the object responsive to the width of the an image of the object and/or the strength of the signals on the two dimensional map. Preferably, the method includes providing electrifying signals to the region from a surface of the region. Preferably, the method includes varying the amplitude of the signals provided from the object.

Preferably, determining the location of the object includes generating a two dimensional map responsive to the measured signals and determining an amplitude of the electrifying signals provided to the object at which at least part of an image of the object on the map is not distinguishable from its surroundings. Preferably, determining the location of the object includes generating a two dimensional map responsive to the measured signals and determining an amplitude of the electrifying signals provided to the object at which at least part of an image of the object is darker than its surroundings on the map and at least part of the image of the object is brighter than its surroundings on the map.

There is further provided in accordance with a preferred embodiment of the present invention, a method for determining the location of an elongate object in a region of a subject, including providing electrifying signals from a part of the elongate object within the region, measuring electrical signals on a surface of the region, generating a map of the region responsive to the measured signals, and changing the electrical signals provided to the elongate object so that the surface signals generated by the elongate object are lower than surrounding surface signals on the map at a first portion of the map and higher than surrounding signals on the map at a second portion of the map.

Preferably, changing the electrical signals includes changing the amplitude of the signals. Preferably, determining the location of the object includes determining the depth of the object responsive to the determined amplitude.

There is further provided in accordance with a preferred embodiment of the present invention, a method of guiding an elongate object within a region of a subject, including providing electrifying signals to the region measuring electrical signals incident on the elongate object within the region, and determining desired movements of the object responsive to the measured signals. Preferably, providing electrifying signals includes providing signals from a surface of the region.

There is further provided in accordance with a preferred embodiment of the present invention, an apparatus for impedance imaging of a region within a body, including a first multi-element probe, including a plurality of sensing elements, for positioning on one side of the region, a second multi-element probe for positioning on a second side of the region and for generating signals to be sensed by the first multi-element probe, and a controller which electrifies fewer than all of the elements of the second multi-element probe.

Preferably, the controller initiates measuring of a signal at less than all of the elements of the first multi-element probe. Preferably, the controller electrifies less than ten percent of the elements of the second multi-element probe concurrently. Preferably, the controller applies concurrently to different ones of at least some of the elements, at least two electrifying signals with different phases. Preferably, the controller applies concurrently to at least some of the elements, at least two electrifying signals with substantially opposite polarity. Preferably, at least some of the elements of the first multi-element probe are allowed to float electrically. Preferably, at least some of the elements of the first multi-element probe are held at an equipotential level. Preferably, the elements of the second multi-element probe include long and narrow straight elements. Preferably, the controller sequentially electrifies different groups of the elements of the second multi-element probe. Preferably, the sequentially electrified groups form long and narrow patterns. Preferably, the probes are cup shaped.

There is further provided in accordance with a preferred embodiment of the present invention, an apparatus for impedance imaging of a region, including a first, multi-element, probe, including a plurality of sensing elements, for positioning on one side of the region, and a second probe which applies electrifying signals which form a dipole, to the region.

Preferably, the second probe includes two groups of elements of substantially equal extent which provide signals of opposite polarity. There is further provided in accordance with a preferred embodiment of the present invention, an apparatus for impedance imaging of a region, including an electrifying probe which applies a plurality of distinct electrifying signals to the region, and a sensing probe, including a two dimensional array of sensing elements which sense signals generated responsive to the plurality of distinct electrifying signals. Preferably, the plurality of distinct electrifying signals are of substantially the same frequency and/or amplitude. Preferably, the plurality of distinct electrifying signals have different phases.

There is further provided in accordance with a preferred embodiment of the present invention, an apparatus for impedance imaging of a region, including a plurality of electrodes for applying electrifying signals to the region, and a probe, including a plurality of sensing elements for sensing signals induced by the applied signals.

Preferably, the plurality of electrodes include at least one first electrode which applies currents to the region and at least one second electrode which attracts currents from the region. Preferably, the at least one second electrode and the at least one first electrode are adapted to be positioned on opposite sides of the region. Preferably, the probe includes at least one sensing element having a high input impedance. Preferably, the probe includes at least one sensing element having a low input impedance. Alternatively or additionally, the probe includes at least one sensing element having a controllable input impedance.

There is further provided in accordance with a preferred embodiment of the present invention, apparatus for sensing electrical signals from a tissue surface, including at least one contact surface suitable for contact with the tissue surface, and a sensing circuit with a controllable input impedance, which senses electrical signals incident on the at least one contact surface. Preferably, the sensing circuit includes one or more switches which select one of a plurality of predetermined input impedance values.

There is further provided in accordance with a preferred embodiment of the present invention, an apparatus for impedance imaging of a region within a body, including a probe including electrifying elements capable of electrifying the region, a multi-element probe, including a plurality of sensing elements, capable of being positioned on one side of the region and circuitry capable of determining at least one characteristic of an anomaly in a region responsive to signals measured by at least some of the sensing elements and the positions of the electrifying elements. Preferably, the circuitry includes dedicated hardware.

Preferably, the circuitry includes a general purpose processor and compatible software. Preferably, the electrifying probe is mounted on an invasive tool inserted into the region. Alternatively or additionally, the multi-element probe is mounted on an invasive tool inserted into the region. Preferably, the circuitry generates a current tracing map responsive to the measured signals. Preferably, the circuitry normalizes the current tracing map. Preferably, the circuitry normalizes the map by subtracting an expected map from the generated map.

Alternatively or additionally, the circuitry normalizes the map by subtracting from the measured signals of at least one group of elements a representative value of the group. Preferably, the circuitry is capable of determining whether an anomaly exits in the region. Alternatively or additionally, the circuitry is capable of determining a position of the anomaly in the region and/or a medical diagnosis of the anomaly.

There is further provided in accordance with a preferred embodiment of the present invention, a method of impedance imaging of a region, including positioning a probe, including a plurality of sensing elements, on a surface of the region, simultaneously applying electrifying signals at a plurality of distinct frequencies to the region, and measuring electrical signals by at least some of the sensing elements responsive to the applied electrifying signals.

Preferably, the method includes determining the separate influence on the region, of the signals of at least one of the distinct frequencies responsive to the measured signals.

Preferably, applying the electrifying signals includes applying the distinct frequency signals to a same electrifying element. Alternatively or additionally, applying the electrifying signals includes applying the distinct frequency signals to different electrifying elements.

Preferably, measuring the electrifying signals by the sensing elements includes sampling the signals adjacent the sensing elements a predetermined number of times and wherein the number of distinct frequencies includes substantially the maximal number allowed by the predetermined number of samplings according to Nyquist's law. Preferably, the method includes selecting a plurality of beginning frequencies and adjusting the frequencies so as to fit into nearest vacant Nyquist bins in order to receive the distinct frequencies. Preferably, selecting the plurality of beginning frequencies includes selecting based on physiological characteristics of the region.

Preferably, adjusting the frequencies includes adjusting low frequencies before high frequencies. Preferably, applying electrifying signals at a plurality of distinct frequencies includes applying signals at frequencies only within a narrow band in which impedance measures do not change substantially. Preferably, the narrow band covers is narrower than 1000 Hz. Preferably, the method includes generating separate maps for a plurality of the distinct frequencies responsive to the measured electrical signals. Preferably, generating the separate maps is performed using a single FFT operation. Preferably, the distinct frequencies are selected so as to allow generating the separate maps using the single FFT operation.

BRIEF DESCRIPTION OF THE DRAWINGS

The present invention will be more clearly understood from the following detailed description of preferred embodiments of the invention and from the attached drawings, in which same number designations are maintained throughout the figures for each element and in which.

DETAILED DESCRIPTION OF PREFERRED EMBODIMENTS

Figure 1:
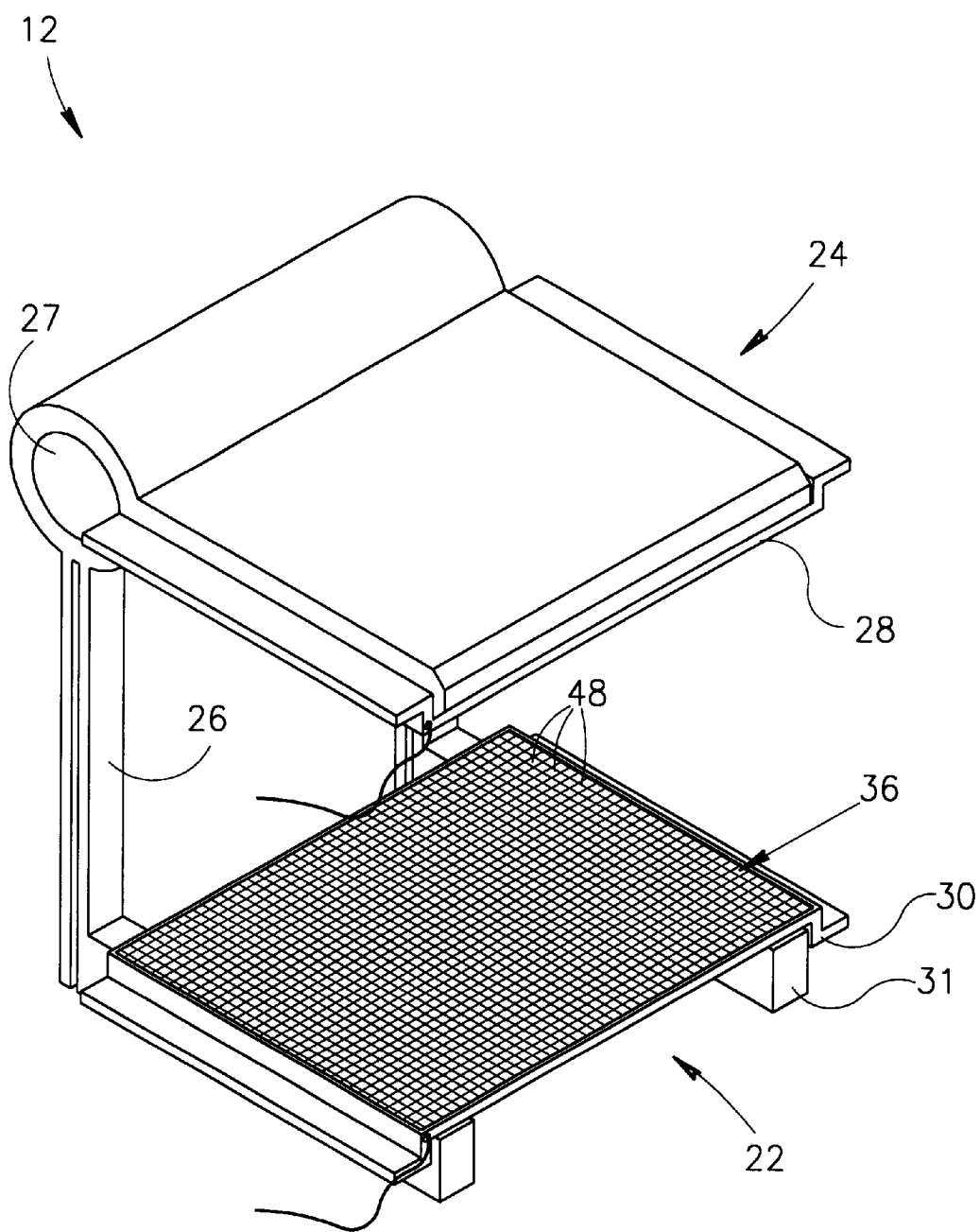
FIG. 1 is a perspective view of an imaging head suitable for breast impedance mapping in accordance with a preferred embodiment of the invention.

FIG. 1 illustrates an impedance image head 12 suitable for mapping the impedance of a breast, in accordance with a preferred embodiment of the present invention. Head 12 preferably comprises a lower plate probe 22 and an upper plate probe 24. The lower or upper plate (or both) is preferably mounted on a pair of rails 26 to allow the distance between plate probes 22 and 24 to be varied. Movement of probe 22 along rails 26 may be achieved by a motor (not shown) or by hand.

Either or both of plate probes 22 and 24 are provided with multi-element probes 28 and 30 respectively, which electrically contact the breast with a plurality of sensing elements 48. Sensing elements 48 are used to provide electrical excitation to the breast and/or to measure signals generated responsive to the provided excitation. Preferably, sensing elements 48 are organized in a two dimensional array. Probes 28 and 30 are preferably as described in U.S. Pat. No. 5,810,742, although other types of probes may be used.

In some preferred embodiments of the present invention, the elements 48 of probe 30 provide electrical excitation and elements 48 of probe 28 measure signals responsive to the provided excitation. Alternatively or additionally, in a first stage, elements 48 of probe 30 provide electrical excitation and elements 48 of probe 28 measure the signals, and in a second stage the elements 48 of probe 30 measure signals and elements 48 of probe 28 provide the electrical excitation. Further alternatively or additionally, some of elements 48 of a single probe 28 and/or 30 provide electrical excitation while, simultaneously, other elements 48 of the same probe measure the signals. Further alternatively or additionally, excitation is provided from a third, possibly remote point, and both probes 28 and 30 sense the resultant signals, concurrently and/or sequentially.

In some preferred embodiments of the present invention, elements 48 are electrified using multi-frequency transmitters and the signals which elements 48 sense are received by a multi-frequency receiver. Thus, a plurality of different scanning steps using different frequencies may be performed simultaneously. It is noted that the human body responds linearly to the signals, i.e., does not mix signals of different frequencies. In a preferred embodiment of the present invention, each electrification step is performed by electrifying the same elements with signals of a combination of frequencies. In a preferred embodiment, signals of different frequencies are applied to different groups of elements 48. Alternatively or additionally, signals combined from a few different frequencies are applied to one or more elements 48.

In a preferred embodiment of the present invention, the multi-frequency signals are applied using a look up table which prepares the digital values of the signals and an analog to digital converter.

The number of different frequencies used concurrently depends on the number of samplings performed by those elements 48 which are used for sampling. In a preferred embodiment, the number of distinct frequencies x is the maximal allowed by Nyquist's law. According to Nyquist's law, if N samplings of each element 48 are used in preparing an image, the maximal value of x is N/2. However, since the amplitude of the DC frequency cannot be determined. Therefore, in a preferred embodiment $x=N/2-1$.

In a preferred embodiment of the present invention, the x frequencies to be used simultaneously are selected so as to allow fast conversion of the sampled signals into frequency distinct maps. Preferably, the x frequencies are chosen in a manner which allows the sensed signals to be converted into a plurality of frequency distinct images using a single Fast Fourier Transform (FFT).

Preferably, each of sensing elements 48 is controlled separately (or the elements are controlled in groups) such that at any single moment some of elements 48 may measure signals, others may provide excitation, and still others may be passive. Further preferably, elements 48 which provide excitation may be driven separately, such that at a single moment different elements 48 of probe 30 provide signals at different amplitudes, frequencies and/or relative phases. Alternatively or additionally, groups of elements 48 forming predetermined shapes on probe 30, are driven together. In a preferred embodiment of the present invention, elements 48 in a single column 36 (or in a single row) are controlled together.

Alternatively or additionally, probe 30 comprises an array of elements of the sizes and/or shapes in which the electrifying signals are to be applied. In a preferred embodiment of the present invention, probe 30 comprises a one-dimensional array of elongated elements. Alternatively or additionally, probe 30 comprises elements of other shapes useful in applying the signals, such as, radial and/or sectorial elements. In some preferred embodiments of the present invention, probe 30 is not necessarily rectangular, but rather is of another shape, such as a circular shape, in order to conform to the shape of the elements.

Head 12 is preferably provided with a pivot (not shown) to allow for arbitrary rotation of the head about one or more of its axes. This allows for both medio-lateral and cranio-caudal maps of the breast to be acquired, at any angular orientation about the breast. Head 12 may be tilted so that the surfaces of plate probes 22 and 24 are oriented with a substantial vertical component so that gravity assists the entry of the breast into the space between the maximum extent and to keep it from inadvertently falling out. This is especially useful when the patient leans over the plates so that her breasts are positioned downwardly between the plate probes.

In a preferred embodiment of the present invention, one or both of probes 28 and 30 may be rotated about an axis at one end thereof, by a rotation mechanism 27 on their associated plate probes 22 or 24, such as shown in FIG. 1 for probe 28. Alternatively or additionally, probes 28 and/or 30 may be slidable, as for example along members 31.

Such additional sliding and rotating flexibility is useful for providing more intimate skin contact of the probes with the breast, which has a generally conical shape. Furthermore, such flexibility allows for better imaging of the areas of the breast near the chest wall or the rib cage, which are extremely difficult to image in x-ray mammography.

In practice, a breast is inserted between probes 28 and 30 and plate probe 22 is raised, or plate probe 24 is lowered, to compress the breast between the probe. This compression reduces the distance between the probes and provides better contact between the sensing elements and the skin of the breast. Although compression is desirable, the degree of compression required for impedance imaging is much lower than required for X-ray mammography. Alternatively or additionally, probes 28 and/or 30 are curved to conform with the surface of the breast in a non-planar fashion.

It is noted that for reasons of clarity, FIGS. 2, 4A, 4B, 4C and 6 show a gap between breast 40 and probes 28 and 30. This gap is not normally existent during impedance imaging procedures.

An imaging procedure preferably comprises a plurality of stages. In a first stage, the breast is scanned in order to determine whether there is a suspected anomaly within the breast. A preferred method for performing the scanning of the first stage is described hereinbelow in relation to FIGS. 2 and 3A–3C. In a second stage, the precise location of the suspected anomaly is found, in particular the depth of the anomaly from either or both of probes 28 and 30. A preferred method for determining the depth is described hereinbelow with reference to FIGS. 4A–4C. In a third stage, electrification measurements are used to determine the type of the anomaly, i.e., whether the anomaly is cancerous or otherwise requires treatment. If the tests of the third stage indicate that invasive tests of the anomaly are required, a forth stage is preferably performed in which impedance imaging is used to direct an invasive tool, such as a biopsy needle, toward the anomaly. A preferred method for leading an invasive tool toward the anomaly is described hereinbelow with reference to FIG. 7.

Figure 2:
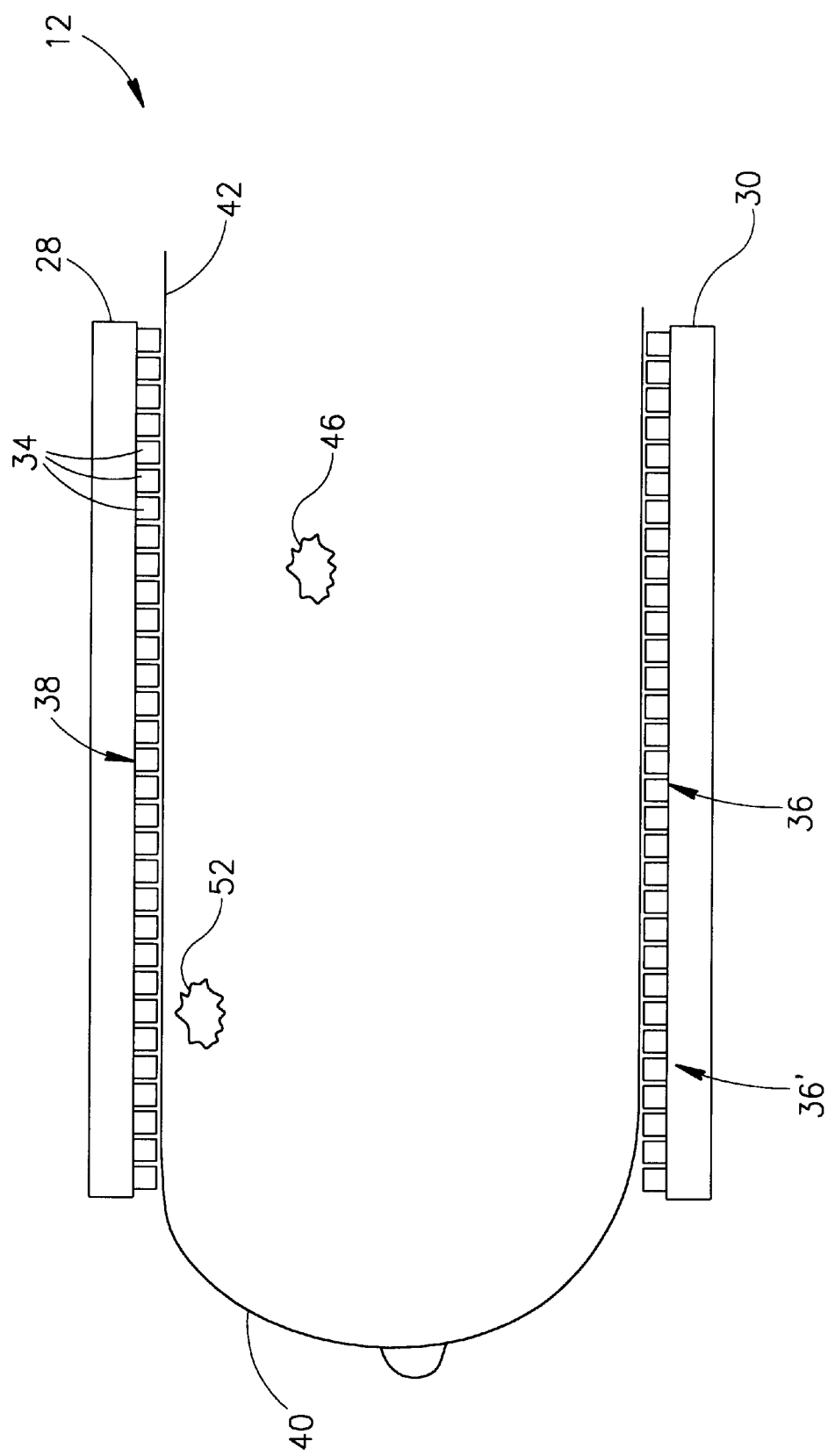
FIG. 2 is a schematic side view of the imaging head of FIG. 1 during an imaging procedure, in accordance with a preferred embodiment of the present invention.

FIG. 2 is a schematic side view of impedance imaging head 12 during an imaging procedure of a breast 40, in accordance with a preferred embodiment of the present invention. Preferably, the imaging procedure comprises a plurality of steps in which one or more elements 48 of probe 30 apply electrical excitation to breast 40. In a preferred embodiment of the invention, probe 28 is kept at a (virtual) ground voltage level, or another equipotential, such that electrical current flows from the electrified elements 48 of probe 30 towards probe 28. Substantially all of elements 48 of probe 28 (referred to herein as sensors 34) sense the electrical signals reaching a surface 42 of breast 40, and a two dimensional map of these electrical signals is prepared (this map is referred to herein as a current tracing map).

In a preferred embodiment of the present invention, one or a few closely spaced sensing elements on one of the probes is electrified, and the others are left floating. This would cause a beam-like flow of current from the electrified elements to the other sensing elements on the other probe. The anomaly would disturb this flow causing impedance variations which are strongest for those elements which are in the path of the current disturbed by the object. If a number of such measurements are made, each with a different group of electrodes being electrified, then good information regarding the three dimensions of the position of the object can be obtained.

Preferably, the applied electrical signals comprise voltage and/or current signals suitable for impedance imaging of breast 40, as described for example in U.S. Pat. No. 5,810, 742. In a preferred embodiment of the present invention, the signals are of frequencies of up to a few MHz. Alternatively or additionally, the applied signals comprise DC signals.

In a preferred embodiment of the present invention, in each step of the imaging procedure a different column 36 of elements 48 is electrified, while the rest of elements 48 of probe 30 are left floating. Preferably, during an entire imaging procedure each column 36 is electrified once. For example, columns 36 are electrified sequentially from left to right or from right to left in FIG. 2. In a preferred embodiment of the present invention, those columns 36 which are far from a suspected anomaly are skipped.

Alternatively or additionally, elements 48 of probe 30 are electrified in other groups, such as along rows perpendicular to columns 36, along diagonal lines, and/or in concentric circles or ellipses. In a preferred embodiment, the groups do not include common elements 48. Preferably, each element 48 is included in at least one group. Preferably, each of the groups covers only a small area of probe 30, preferably less than 10% of the probe.

Applying signals from a small area relative to the area of probe 28 at which the signals are sensed, makes signals from surface anomalies close to sensing probe 28 (which are generally less interesting) interfere less with signals from a deep anomaly, the location of which is being determined. In addition, the sensed signals which are indicative of the deep anomaly vary according to the position of the electrifying group, while the signals indicative of the surface anomaly which is close to probe 28 do not change with the position of the electrifying group.

Figure 3A:
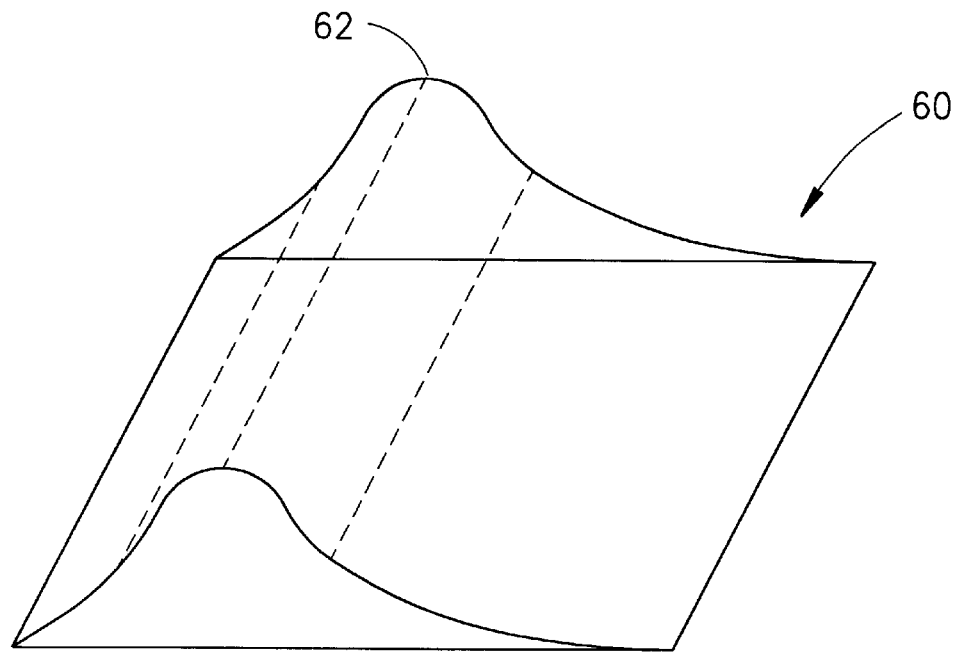
FIG. 3A is a two-dimensional schematic graph of current sensed from a healthy breast, in accordance with a preferred embodiment of the present invention, when the breast is electrified by a linear dipole.
Figure 3B:
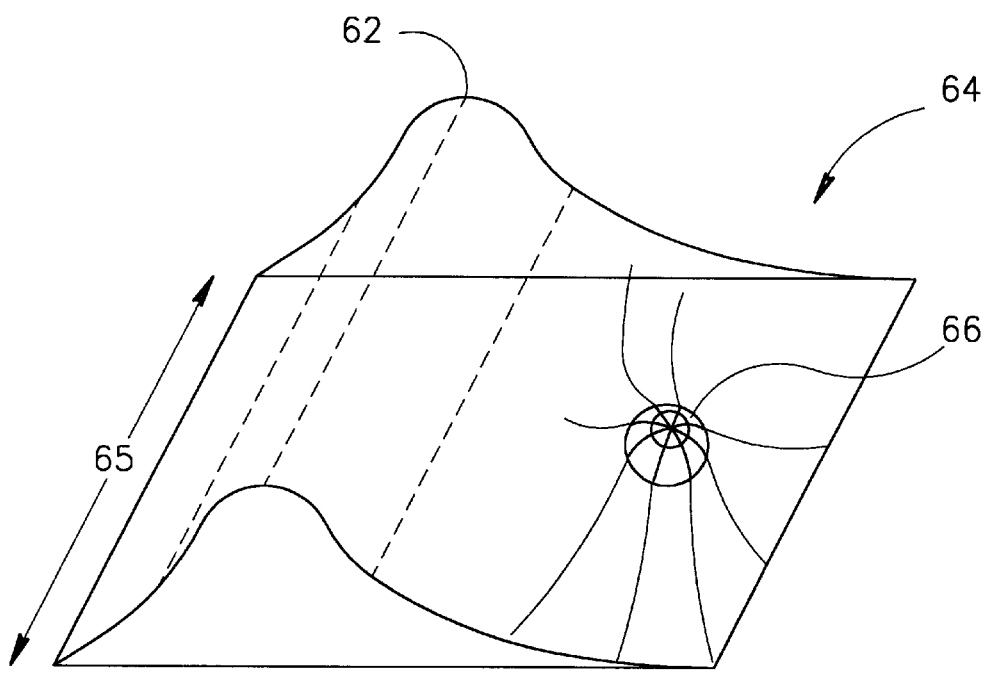
FIG. 3B is a two-dimensional schematic graph of signals sensed from a breast with an anomaly, in accordance with a preferred embodiment of the invention, under conditions similar to those of FIG. 3A.

Reference is also made to FIGS. 3A and 3B which are two-dimensional schematic graphs 60 and 64 of the current sensed by probe 28, in accordance with a preferred embodiment of the present invention. FIGS. 3A and 3B show graphs sensed from breast 40 when electrifying signals are applied along a line 36' of elements 48 (FIG. 2). Graph 60 in FIG. 3A shows the signals sensed from a healthy breast. The current sensed by sensors 34 of probe 28 (FIG. 2) is inversely proportional to the distance between the sensors and the electrifying elements along line 36'. Therefore, graph 60 has a peak 62 along a line parallel to line 36' which declines as the distance from line 36' increases. Graph 60 has substantially identical values along lines parallel to line 36' due to the regularity of the tissue of a healthy breast 40.

Graph 64 in FIG. 3B shows the current sensed from a breast which has an anomaly 46 within it. The impedance of the tissue of anomaly 46 is substantially different from the impedance of the healthy tissue of breast 40. The electric field caused by the current from line 36' induces a dipole within anomaly 46. Therefore, in addition to a peak 62 similar to the one in graph 60, graph 64 includes a peak 66 induced by the dipole in anomaly 46. The heights of peaks 62 and 66 depend on the amplitudes and frequencies of the signals applied along line 36', as well as on the tissue characteristics of anomaly 46. The height and width of peak 66 also depends on the depth of anomaly 46 within breast 40. This is because the electric field of anomaly 46 declines with the third power of the distance between anomaly 46 and surface 42. The height of peak 66 also depends on the induced dipole moment of anomaly 46. In a preferred embodiment, the dipole moment of anomaly 46 is estimated from the type and/or shape of the anomaly. The depth of anomaly 46 within breast 40 is preferably determined based on the estimated dipole moment and on the relative height of peak 66 relative to peak 62. Alternatively or additionally, anomaly 46 is assumed to have a regular spherical shape.

In some preferred embodiments of the present invention, impedance graphs 64 are generated on both probes 28 and 30 and the depth of anomaly 46 is estimated from the relative heights of peaks 66 on the opposing graphs. In a preferred embodiment, the sensing elements of one of probes 28 and 30 are all electronically floating and are not in use, while the elements of the other of probes 28 and 30 operate as sensors, and a remote signal source is used to electrify breast 40. After an image is obtained from the one probe, the roles of the two probes 28 and 30 are reversed to obtain an image from the other probe.

Alternatively, if all the elements 48 of one of the probes are electrified to the same voltage and the measuring probe is kept at a virtual ground, the currents drawn from and received by the elements of both probes form a two dimensional admittance image of the region between the probes.

Preferably, the graph sensed by probe 28 is normalized in a manner which eliminates the effects resulting directly from line 36'. In some preferred embodiments of the present invention, currents which appear along the entire length 65 of graph 64 are subtracted from the graph. Since it is reasonable to assume that anomaly 46 does not extend along the entire length of lines 36, currents which appear along the entire length 65 of graph 64 are not indicative of anomaly 46 and generally result directly from line 36'. Preferably, a normalizing value is subtracted from the values of each line 38 of sensors 34 parallel to lines 36. Preferably, the normalizing value for each line 38 comprises the average or mean value sensed along line 38. Alternatively, the normalizing value comprises the minimum value sensed by any of the sensors 34 along line 38. The minimum value is common to all the sensors 34 along the line and therefore does not result from anomaly 46. In a preferred embodiment of the present invention, when an anomaly 46 is detected, either automatically or by a physician, the normalizing value is an average of the values along lines 38 of those points which do not belong to the anomaly.

Alternatively, an expected set of values for healthy tissue is subtracted from graph 64. Further alternatively or additionally, standard image processing techniques, such as low pass filtering, are applied to the graph to prepare it for inspection by a physician.

Figure 3C:
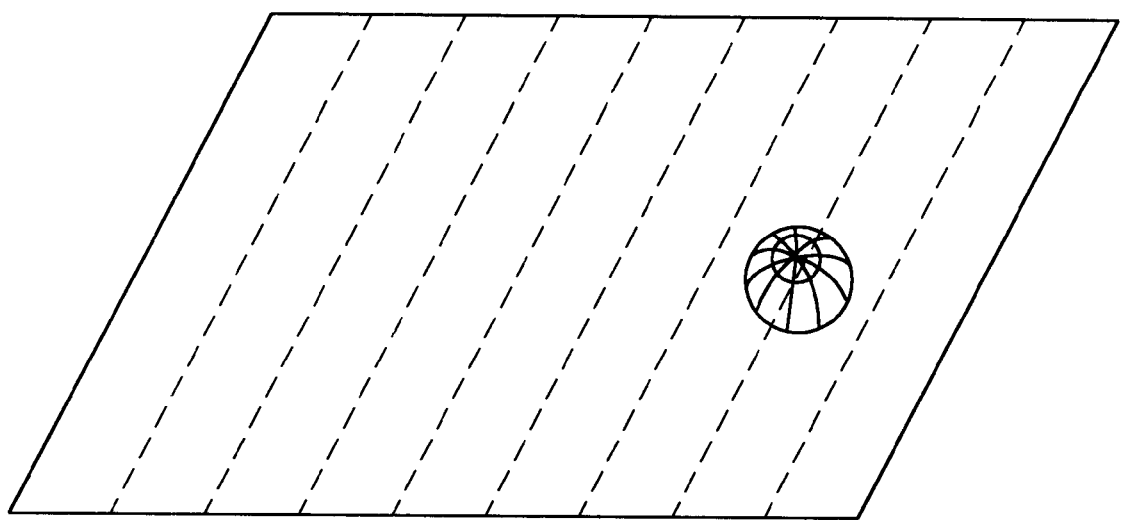
FIG. 3C is a schematic normalized graph of the graph of FIG. 3B, in accordance with a preferred embodiment of the present invention.

FIG. 3C is a normalized graph of graph 64 of FIG. 3B designating the current sensed by probe 28 originating from anomaly 46, in accordance with a preferred embodiment of the present invention.

The normalized graph is preferably displayed on a screen (not shown) to be analyzed by a physician searching for tumors which are suspected as being malignant. Conventionally, the normalized graphs are displayed as a two dimensional map in which brighter shades signify areas in which high current levels were received while dark shades signify areas which received less current. Usually, most of breast 40 appears as an area with the same shade and anomalies stand out as much brighter areas.

As described above, in some preferred embodiments of the invention, an imaging session includes a plurality of steps in which normalized maps of breast 40 are generated based on applied signals along different lines 36.

In a preferred embodiment of the present invention, each of the normalized maps is displayed separately for inspection by the physician. Alternatively or additionally, the normalized maps are automatically analyzed separately using signal processing methods, by a processor associated with image head 12. The analysis preferably includes determining whether an anomaly exists in breast 40 and/or the location and depth of the anomaly. The results of the analysis are preferably displayed together with the respective maps, or in the form of a table summarizing substantially all the normalized maps. Alternatively or additionally, the analysis includes choosing (for display) one or more maps which best depict possible anomalies in breast 40. For example, the analysis may choose for displaying one or more maps in which the contrast between points within a small area is larger than a predetermined value.

It is noted that the current originating directly from elements 48 interfere with the detection of the current from anomaly 46. Generally, when more current is generated by probe 30 the detection of weak signals from anomalies far from probe 28 becomes harder. When elements 48 are electrified in a two-dimensional array, the strength of the signals substantially does not decrease with distance. When the elements are electrified in a one-dimensional array the signals decrease proportionally to the distance, and less interfere with the signals from anomaly 46. Therefore, it is desired to reduce the dimensionality of the applied signals. Furthermore, in many cases, signals from surface anomalies interfere with signals from a deep tumor which is to be detected. In such cases, the deep tumor is more readily identified when electrifying fewer elements 48 (FIG. 2).

For example, if a surface anomaly 52 is located on surface 42 it will form a dipole similar to the dipole formed in anomaly 46 which is to be detected. When a uniform electrical field is applied to probe 30 anomaly 46 and surface anomaly 52 form dipoles of substantially the same strength. On the other hand, the effect of anomalies 46 and 52 on sensors 34 is always dependent on the distance between the respective anomalies and sensors 34. Since the dipole in surface anomaly 52 is closer to sensors 34 than anomaly 46, surface anomaly 52 has a stronger effect in the sensors than anomaly 46. By electrifying only a single line 36 on probe 30, the electric field within breast 40 decays proportionally to the distance from probe 30 and therefore the effect of anomaly 46 relative to surface anomaly 52 increases.

The dimensionality of the applied signals is reduced even more by using applied signals which interfere with each other, for example by electrifying two parallel lines 36 with opposite phases. The reduction of the dimensionality is especially important in the stage of determining the exact location of anomaly 46, especially the depth of the anomaly.

Figure 4A:
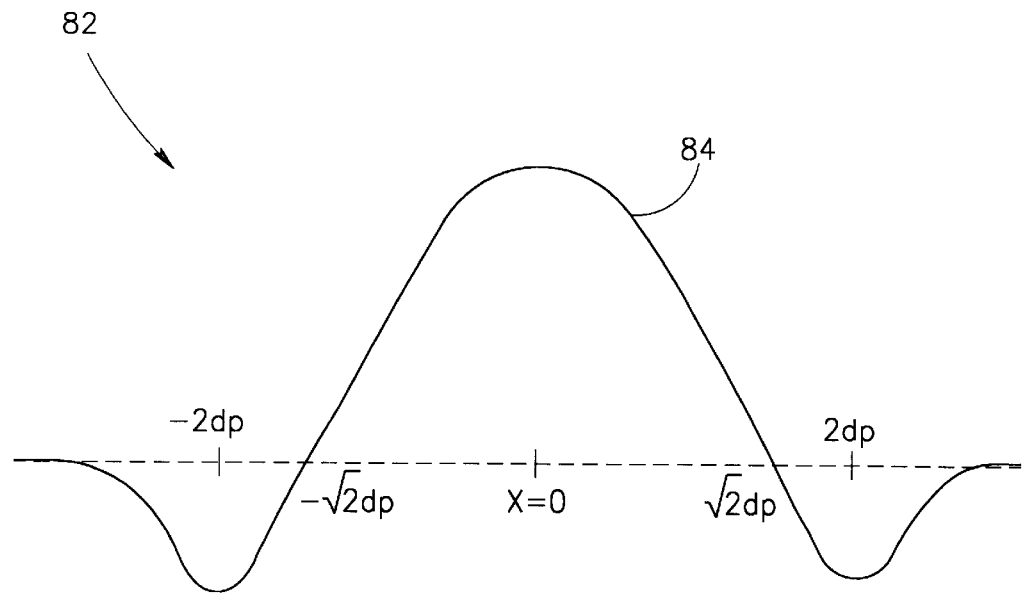
FIGS. 4A–C are schematic illustrations of an imaging stage using electrifying elements forming a dipole in which an anomaly is at different locations relative to the dipole, in accordance with another preferred embodiment of the present invention.
Figure 4A:
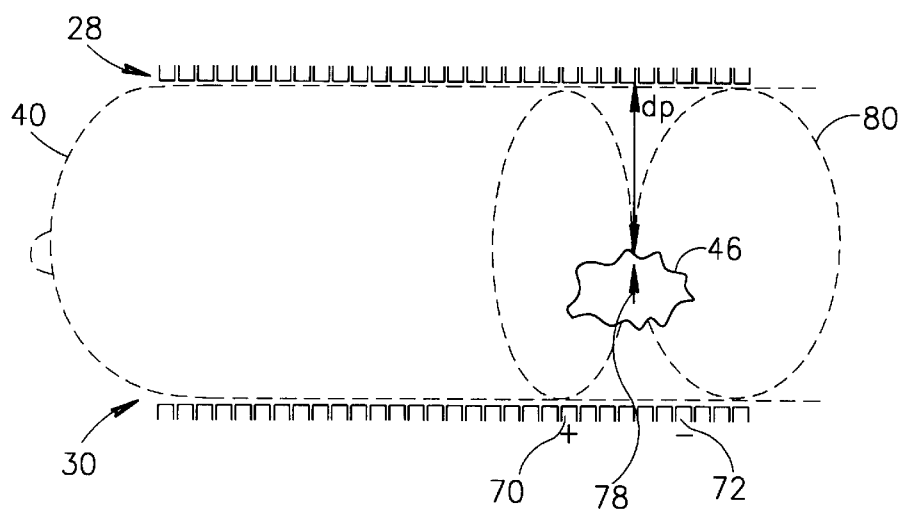

FIG. 4A is a schematic illustration of a first step of an imaging stage for determining the depth of anomaly 46, in accordance with a preferred embodiment of the present invention. Preferably, after anomaly 46 is found, a dipole is induced within anomaly 46, as indicated by an arrow 78. The dipole in anomaly 46 induces within breast 40 an electrical field indicated by dashed lines 80. In a preferred embodiment of the present invention, the dipole is induced by applying electrifying signals of different phases, e.g., opposite polarities, to a pair of lines 70 and 72 on opposite sides of the projection of the anomaly on probe 30, such that the center between lines 70 and 72 is located beneath the center of anomaly 46.

In a preferred embodiment of the present invention, the depth determining stage begins with applying positive signals to line 70 without applying signals to line 72, i.e., applying negative signals of a zero amplitude. This electrification results in the dipole of anomaly 46 being pointed toward probe 28 (with a slight angle to the right which is negligible), as illustrated in FIG. 4A. The influence of the dipole induced within anomaly 46 on the array of sensors 34 is shown schematically by a graph 82. Graph 82 is a cross section of the normalized map formed by sensors 34 taken above anomaly 46. Graph 82 is preferably normalized using any of the normalization methods described above with relation to FIGS. 3A–3C.

Graph 82 includes a single positive peak 84 above anomaly 46 and negative peaks 85 and 86 to the right and left of peak 84, respectively. The height of peak 84 depends on the location and characteristics of anomaly 46 similarly to peak 66 in FIG. 3B. For common anomalies, the height of peak 84 is about twice the background height (not shown, as the background was removed in the normalization). Designating the point above anomaly 46 as x=0, and the depth of anomaly 46 within breast 40, i.e., the distance between anomaly 46 and probe 28, as dp, peak 84 zeros approximately at x=±√2 dp, at which points negative peaks 85 and 86 begin. Peaks 85 and 86 have a maximal magnitude at about x=±2 dp from which points they substantially monotonously decay to −0 at infinity.

A negative signal of gradually increasing amplitude is preferably applied to line 72 while the amplitude on line 70 remains constant, resulting in the rotation of the dipole in anomaly 46.

Figure 4B:
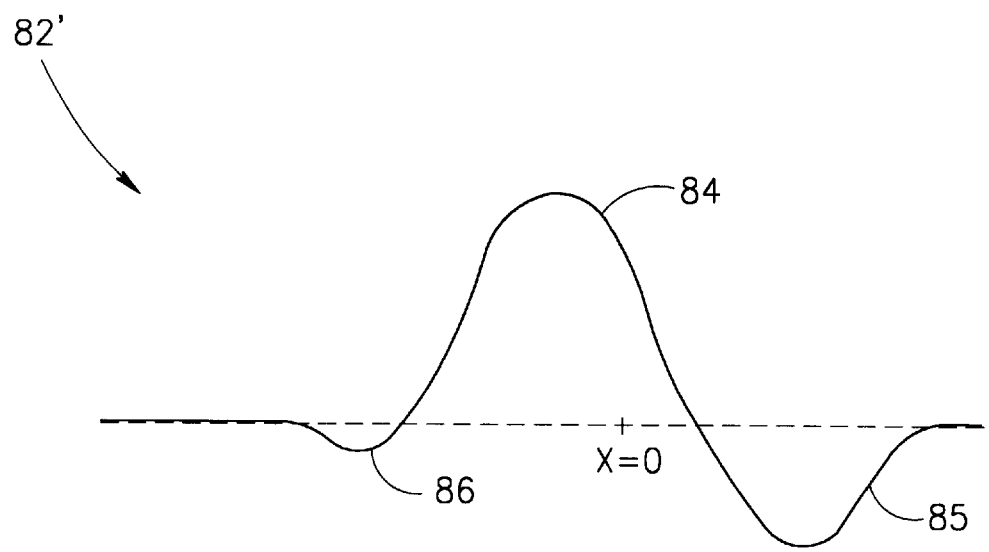
Figure 4B:
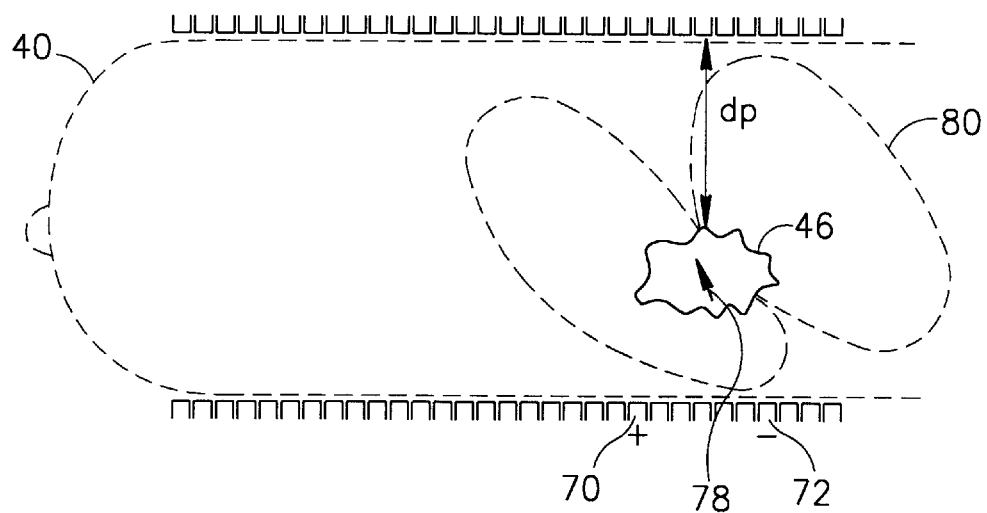

FIG. 4B is a schematic illustration of an imaging step in which the dipole within anomaly 46 forms an angle relative to probes 28 and 30. Accordingly, field lines 80 also form an angle relative to probes 28 and 30. The influence of the dipole within anomaly 46 on the array of sensors 34 is shown schematically by a graph 82' in a manner similar to graph 82 of FIG. 4A. As the direction of the dipole indicated by arrow 78 tilts to the left, peaks 84, 85 and 86 move to the left, the magnitude of peak 85 on the right of peak 84 increases (i.e., becomes more negative), and the magnitude of peaks 84 and 86 decrease. Thus, the heights of peaks 84, 85 and 86 depend on the direction of the dipole within anomaly 46.

It is noted that peaks 84, 85 and 86 do not run along the entire length of probe 28 (into the page of FIGS. 4A and 4B) but rather exist only around the position of anomaly 46.

The amplitude of the signals applied to the elements along line 72 is preferably increased until the direction of the dipole within anomaly 46, indicated by arrow 78 is substantially parallel to probe 30. Generally, the dipole within anomaly 46 is parallel to probe 30 when the amplitudes of the signals applied to lines 70 and 72 are substantially equal. It is noted, however, that this general rule may not be accurate, for example, due to inaccuracies in selection of lines 70 and 72. At this point, the distance between peaks 84 and 85 is preferably used to determine the depth dp of anomaly 46.

Figure 4C:
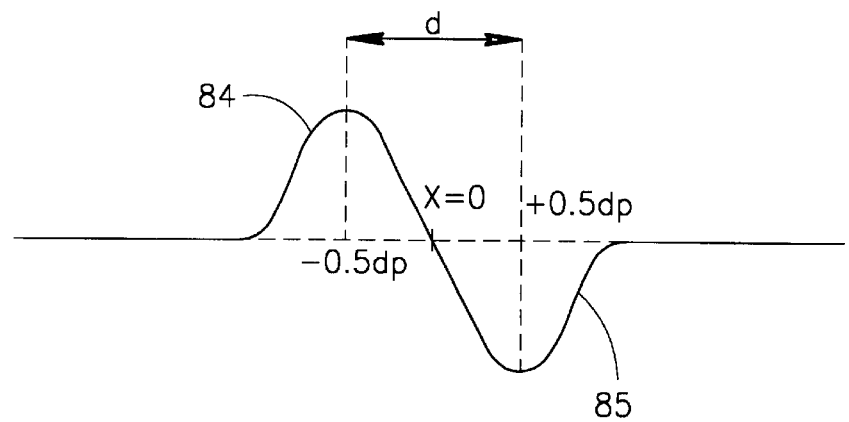
Figure 4C:
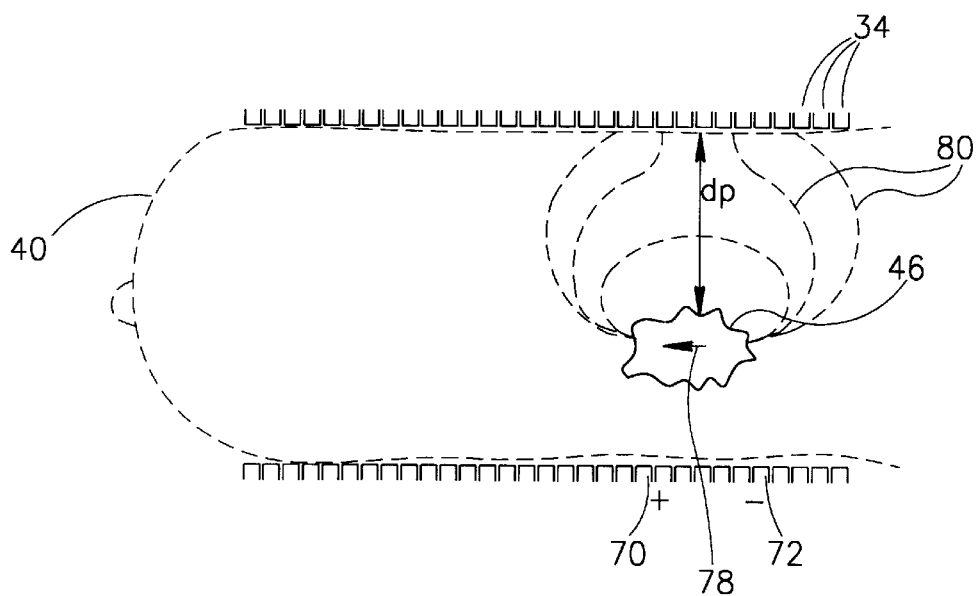

FIG. 4C is a schematic illustration of an imaging step in which the dipole within anomaly 46 is substantially parallel to probe 28. When the dipole within anomaly 46 is parallel to probe 28, peak 86 disappears and peaks 84 and 85 are of substantially equal magnitude, located anti-symmetrically around the point x=0 which is directly above anomaly 46. The distance d between peaks 84 and 85 is a function of the depth dp of anomaly 46 in breast 40, and of the size of anomaly 46. For anomalies of common sizes which are smaller than the depth dp, the distance d is substantially equal to depth dp. It is noted that for larger anomalies peaks 84 and 85 are smeared.

Preferably, the signals applied to lines 70 and 72 are interchanged and the above process is repeated. In some cases it is easier to detect positive peaks than negative peaks. Therefore, after detecting the precise location of one of peaks 84 and 85 the applied signals are reversed and the precise position of the other of the peaks is determined.

In a preferred embodiment of the present invention, the process of determining the depth of anomaly 46 includes following the movements of peaks 84, 85 and 86. Detection of the peaks is easiest in the state shown in FIG. 4A, and the depth measurement is best performed in the state shown in FIG. 4C. Therefore, in a preferred embodiment of the invention, the depth measurement is performed by gradually changing the signals applied to lines 70 and 72 and following the changes in peaks 84 and 85 until the peaks are of the same size. In a preferred embodiment, the movements of peaks 84 and 85 are induced automatically by a controller which controls the signals applied to lines 70 and 72. Preferably, the controller also determines when peaks 84 and 85 are of equal size. Alternatively or additionally, the determination when peaks 84 and 85 have equal sizes and/or the inducing of the movements of peaks 84 and 85 are performed under manual control oh a physician.

Alternatively or additionally to moving peaks 84, 85 and 86 by gradually changing the direction of the dipole within anomaly 46, the peaks may be moved by other methods, such as by moving the electrification lines 70 and/or 72 along probe 30. In this alternative, lines 70 and 72 with a constant distance between them are preferably passed along probe 30 until peaks 84 and 85 have equal sizes. In a preferred embodiment of the present invention, lines 70 and 72 are passed over probe 30 while having equal amplitudes and substantially opposite polarities, thus forming a dipole between the lines. The dipole formed by lines 70 and 72 induces an electrical field within breast 40, which field induces a counter dipole within anomaly 46, as indicated by arrow 78.

In this alternative, the direction of the dipole within anomaly 46 is a function of the distance between anomaly 46 and lines 70 and 72. When lines 70 and 72 are far from the projection of anomaly 46 on probe 30, the direction of the dipole within anomaly 46 is substantially from probe 30 to probe 28, as shown in FIG. 4A. As the dipole formed of lines 70 and 72 approaches the projection of anomaly 46, the dipole within anomaly 46 rotates until it becomes parallel to probe 30 when the projection of anomaly 46 is substantially between lines 70 and 72.

It is noted that since the electrical field induced by lines 70 and 72 is regular in the dimension parallel to lines 70 and 72, the influence of the field on probe 28 is canceled in the normalizing of the map. Therefore, only the influence due to the dipole within anomaly 46 appears on the maps generated by probe 28. It is also noted that the current due to direct influence from lines 70 and 72 declines proportionally to the square of the distance and therefore interferes to a lesser extent in determining the current from anomaly 46 than current from a single positive line 36 as described above with reference to FIG. 2.

In a preferred embodiment of the present invention, the location of the projection of anomaly 46 on probe 28 is determined, as described above, using the method of FIG. 2 and/or a method in which substantially all the elements of probe 30 are electrified. Alternatively or additionally, the location of the projection of anomaly 46 is determined by electrifying lines 70 and 72 sequentially along probe 30 with a fixed distance between the lines, and finding the positions of lines 70 and 72 for which peaks 84 and 85 have the same magnitude and/or for which peak 86 disappears. Further preferably, breast 40 is scanned a few times with different distances between lines 70 and 72. In a preferred embodiment of the present invention, relatively large distances between lines 70 and 72 are used, in order to enhance the strength of the dipole within anomaly 46. The average point between peaks 84 and 85 is substantially directly above anomaly 46. After the location of the projection of anomaly 46 on probe 28 is determined the depth of anomaly 46 is preferably determined using the method of FIGS. 4A–4C. Thus, the three coordinates of anomaly 46 are determined using a sensing probe 28 which covers only a single side of breast 40, or stated otherwise, covers less than 50%, even 25%, of the total surface area of breast 40.

In another preferred embodiment of the present invention, a first detection stage is performed in which substantially all the elements 48 of probe 30 are electrified. Those areas which show irregularity are scanned using a single line 36, as described with reference to FIG. 2, in a second stage. In a third stage, those anomalies detected in the second stage are examined using pairs of lines with opposite polarity in order to determine the depths of the anomalies. In a preferred embodiment of the invention, the depth is determined from both probes 28 and 30, by alternately using one of the probes for providing electrifying signals and the other one of the probes for sensing the signals.

In some preferred embodiments of the present invention, a plurality of maps for different electrification patterns are prepared concurrently by applying the electrification signals of the different patterns simultaneously, using different frequencies. For example, signals at different frequencies may be applied concurrently to lines 70 or to pairs of lines 70 and 72 concurrently thus scanning the entire region in one or a few electrifying steps. Preferably, the frequencies used are within a relatively narrow band, such that the impedance measure does not differ significantly between the frequencies. For example, frequencies between 1000 Hz and 1600 Hz at steps of 20 Hz may be used to form over 30 maps concurrently.

In a preferred embodiment of the present invention, the estimated depth of anomalies is superimposed on the representation of the anomaly on a map of the breast. Alternatively or additionally, the physician may point (e.g., using a mouse) at an area on the map and responsive thereto the processor displays information on the pointed area including, for example, an approximated depth, and/or a size and shape of an anomaly at the pointed area.

In some preferred embodiments of the present invention, the processor provides the physician with information extracted from a plurality of the normalized maps. In a preferred embodiment, the physician is provided with an output which includes the percentage of maps in which an anomaly was detected. Preferably, the location and depth of the anomaly are determined as a weighted average of the location and depth from all the maps in which it was detected. Preferably, maps generated with applied signals closer to anomaly 46 are given more weight in the weighted average.

Alternatively or additionally, the location and depth of anomaly 46 are determined directly from the normalized graphs of a plurality of steps. Further alternatively or additionally, a superposition graph of some or all of the graphs from different steps is displayed. Alternatively or additionally, only graphs which are determined to be interesting, i.e., are substantially different from expected graphs for healthy breasts, are displayed for examination by the physician.

In a preferred embodiment of the invention, the normalized map displayed to the physician responsive to the method of FIGS. 4A–4C is corrected so as to indicate the point above anomaly 46 instead of peaks 85 and 86. Preferably, peaks 85 and 86 are replaced by a single peak at the center point between peaks 85 and 86. The replacement peak is preferably given a height which is a weighted average of the absolute heights of peaks 85 and 86. Alternatively, the height of the replacement peak is a function of the depth of anomaly 46. Further alternatively, the height of the replacement peak is a predetermined arbitrary value which makes the anomaly appear clearly on the normalized map.

In a preferred embodiment, sensors 34 are kept at a virtual ground level, or at any other equipotential level, which attracts electrical currents from probe 30 towards probe 28. In this embodiment, sensors 34 preferably have a low input impedance. Thus, probe 28 affects the electrical signals being measured. Specifically, only currents perpendicular to probe 28 can exist in the proximity of probe 28 and generally it is easier to detect dipoles which are perpendicular to probe 28 than dipoles which are parallel to probe 28.

Alternatively or additionally, sensors 34 measure the electric signals in a manner which minimizes their influence on the fields. In a preferred embodiment of the present invention, some or all of sensors 34 are connected with a high input impedance. In this embodiment, an electrode separate from probes 28 and 30 (not shown) is preferably attached to breast 40 or to another surface of the patient's body in order to attract the currents applied by probe 30.

In another preferred embodiment, sensors 34 are operated in a low impedance mode but are turned on sequentially rather than concurrently, such that at any single time only a small fraction of sensors 34 influence the field within breast 40. Thus, the field within breast 40 is not forced to be perpendicular to probe 28. It is noted that detecting dipoles which are parallel to probe 28 is much easier when sensors 34 substantially do not influence the field within breast 40.

In a preferred embodiment of the present invention, most of sensors 34 sense voltages while a small fraction of the sensors sense currents and attract the currents from probe 30. In this embodiment the signals are sensed in a single step without the need of an external electrode to attract the currents. In a preferred embodiment, the low impedance sensors are located in the center of probe 30, for example, along a line parallel to lines 70 and 72 or in a central circle or square.

In a preferred embodiment of the present invention, some of sensors 34 have a high input impedance while others have a low input impedance. Thus, in some steps the sensing may be performed with the high input impedance sensors and in other steps the sensing is performed with the low input impedance sensors.

Figure 5:
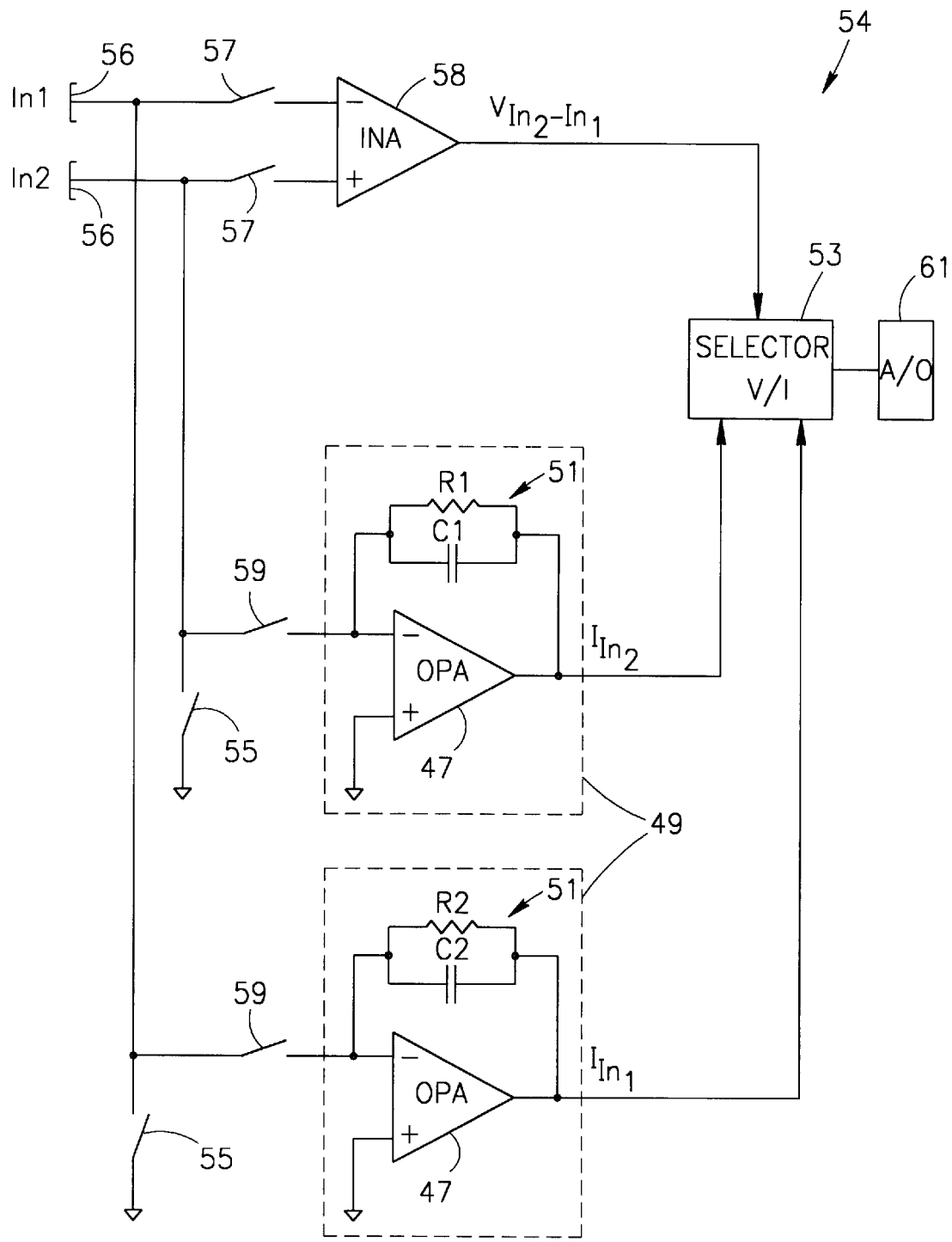
FIG. 5 is a schematic illustration of a sensor, in accordance with a preferred embodiment of the present invention.

FIG. 5 is a schematic illustration of a sensor 54, in accordance with a preferred embodiment of the present invention. Sensor 54 has a controllable input impedance which is changed for different sensing steps as required. Sensor 54 preferably receives input signals from a pair of contacts 56 which contact human surfaces in a manner similar to sensors 34. In a preferred embodiment of the invention, contacts 56 are part of an array of contacts similar to probes 28 and 30. In a preferred embodiment of the invention, a first pair of switches 55 connects contacts 56 to a ground potential. A second pair of switches 57 connects contacts 56 to a voltage measurement amplifier 58 which measures the voltage differential between the contacts 56. Preferably, voltage measurement amplifier 58 has a high input impedance as is known in the art. In a preferred embodiment, voltage measurement amplifier 58 comprises an INA unit, for example, the INA2128 available from Burr Brown.

A third pair of switches 59 preferably connect contacts 56 to current measurement circuits 49, which measure the currents on contacts 56 separately. Current measurement circuits 49 preferably comprise an operational amplifier 47, such as the AD746 available from Analog Devices. Preferably, circuit 49 comprises an impedance circuit 51 parallel to the operational amplifier 47. In a preferred embodiment, impedance circuit 51 comprises a resistor of about 100 kohm and a capacitor of about 47 pF in parallel. The outputs from voltage measurement amplifier 58 and current measurement circuits 49 are preferably passed through a selector 53 to an analog to digital converter 61.

During their operation, each of contacts 56 is preferably in one of four states set by switches 55, 57 and 59. In a first state, contact 56 is connected to amplifier 58 for voltage measurement. Preferably in this state, both of contacts 56 are connected to amplifier 58. In a second state, contact 56 is connected to current measurement circuit 49. In a third state contact 56 is connected to a ground potential in order to generate an equipotential surface while other contacts 56 are measuring currents (or voltages). In a fourth state, contact 56 is left floating (unconnected) preventing the contact 56 from influence measurements performed by other contacts 56.

Preferably, the high impedance input of amplifier 58 is substantially higher than the impedance levels within breast 40. The low impedance input of circuit 49 is preferably substantially lower than the impedance levels within breast 40.

After the position of the anomaly is determined, non-invasive diagnostic methods are preferably used in order to determine the nature of anomaly 46. Preferably, signals of various frequencies and amplitudes are applied beneath the determined area at which anomaly 46 was found in order to generate a diagnostic impedance image of the vicinity of anomaly 46, as described, for example, in above mentioned U.S. Pat. No. 5,810,742.

In a preferred embodiment of the present invention, a plurality of diagnostic images of different frequencies are produced simultaneously, using the method described above. Preferably, the frequencies used in creating the diagnostic images are as close as possible to frequencies which are suitable for physiological considerations while allowing creation of the diagnostic images using a single FFT operation. Alternatively or additionally, the frequencies used in creating the diagnostic images are dispersed evenly on a logarithmic scale of a band of useful frequencies.

In a preferred embodiment of the present invention, x beginning frequencies are selected throughout the useful spectrum (between a few Hz and a few MHz), preferably according to physiological considerations of the tissue of the scanned region. Thereafter, the beginning frequencies are preferably adjusted such that each frequency has a different "alias" in the Nyquist regime, i.e., each frequency occupies a different "bin" in the Fourier spectrum. Preferably, the adjusting begins with the lower frequencies by bringing the lower frequencies to the nearest bins and continues with the higher frequencies which are brought to the nearest of the remaining bins. This is because adjustments in high frequencies are less significant than in low frequencies.

In a preferred embodiment of the present invention, an entire examination session is performed automatically by a processor, based on preprogrammed instructions to probes 30 and 28. The processor preferably determines which elements of probe 30 are electrified in each step and which elements of probe 28 sense the signals, and how. In addition, the processor preferably normalizes the maps sensed by probes 28 and calculates the depth of suspected anomalies, as described above. In a preferred embodiment, the processor also determines whether additional tests are required responsive to results of earlier tests in the session and preferably automatically performs these additional tests. For example, when a suspected dark point of a borderline size is detected, the processor initiates additional tests to determine whether the dark point represents an anomaly which requires a biopsy test. Thus, the physician does not need to intervene with the operation of image head 12.

Alternatively or additionally, the physician manually instructs a controller of image head 12 which imaging steps and/or stages are to be performed and/or sets parameters of the steps and/or stages, such as the distance between lines 70 and 72. Further alternatively or additionally, the physician controls each step of the examination session, including the identities of the elements 48 electrified in each step.

Although the above description refers to a specific embodiment of probes 28 and 30, many other probes may be used to carry sensors 34 and/or to apply the electrifying signals. For example, elements 48 may be mounted on various types of flexible probes. In some preferred embodiments of the present invention, elements 48 are mounted on probes suitable for insertion into the body of a patient so as to apply the electrifying signals and/or sense the resultant signals as close as possible to a suspected tumor. For example, elements 48 may be mounted on a fingertip probe, on a laparoscopic probe, and/or on an intra-operative paddle type probe, as described in the above referenced U.S. Pat. No. 5,810,742. In a preferred embodiment of the present invention, elements 48 are mounted on an invasive tool, such as a biopsy needle, to help lead the tool toward a tumor, as described hereinbelow.

Figure 6:
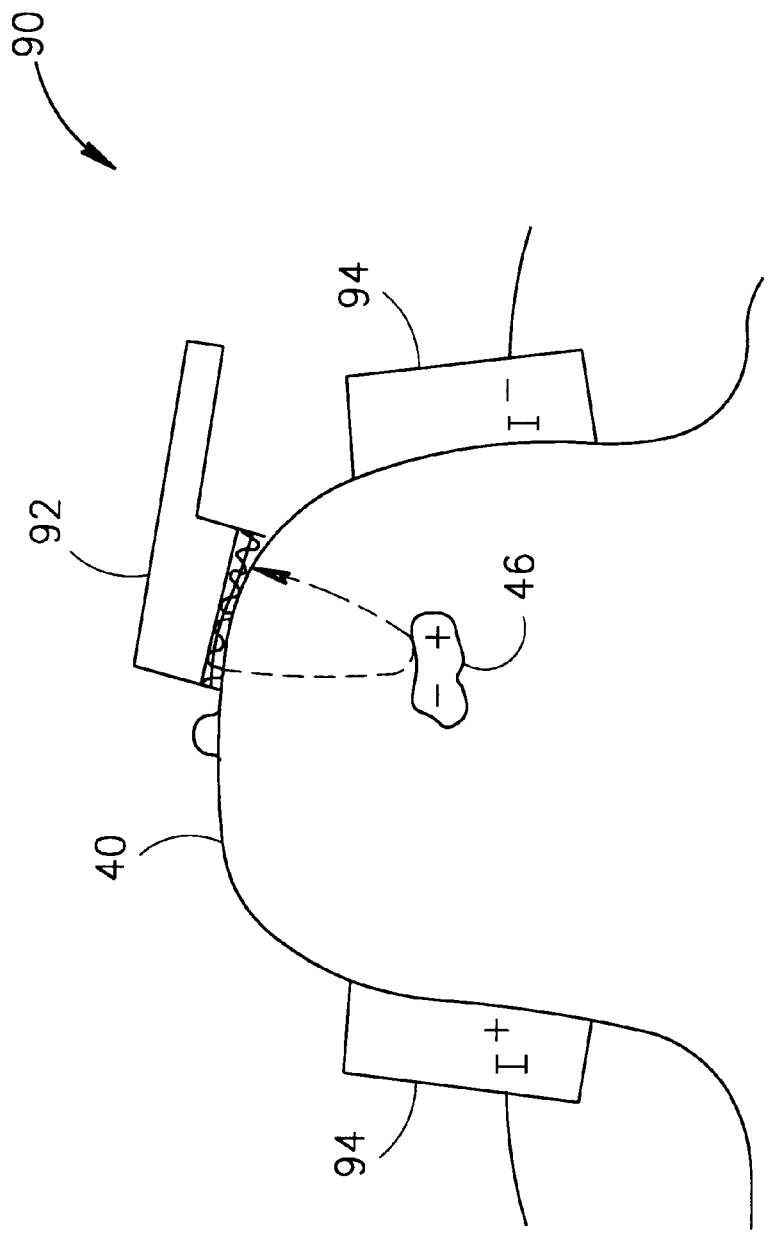
FIG. 6 is a schematic illustration of an impedance imaging system, in accordance with a preferred embodiment of the present invention.

FIG. 6 is a schematic illustration of an impedance imaging system 90, in accordance with a preferred embodiment of the present invention. System 90 comprises a hand held sensing probe 92 and a pair of electrifying probes 94, which are preferably firmly attached to opposite sides of breast 40. The use of a hand held probe 92 for sensing allows a physician to control the position of sensing probe 92 and choose the best location for examining a specific area of breast 40. Furthermore, when the physician desires to insert a biopsy needle or other invasive tool to breast 40, sensing probe 92 is easily moved by the physician to make room for the insertion of the needle.

Electrifying signals are applied to probes 94 in order to induce a dipole within an anomaly 46 located within breast 40. Preferably, electrifying probes 94 operate as current sources of the same magnitudes with opposite phases such that currents flow within breast 40 from one of probes 94 to the other. In a preferred embodiment of the invention, each probe 94 comprises a single element such that the probe applies the same signals from its entire surface. Alternatively, probes 94 comprise arrays of elements in any of the arrangements described with reference to probe 30.

Probe 92 preferably comprises a two dimensional array of sensors as described above with reference to probe 30. In a preferred embodiment of the present invention, the sensors of sensing probe 92 measure the electric signals in a manner which minimizes the influence of sensing probe 92 on the measured signals. The induced currents, therefore, flow primarily between probes 94, inducing a dipole within anomaly 46, and only minimally influencing the measurements of sensing probe 92. Thus, the signals from anomaly 46 are easily detected by sensing probe 92 since the signals are not obscured by the currents flowing between probes 94. Furthermore, the dipole within anomaly 46 is substantially parallel to sensing probe 92 allowing determination of the depth of anomaly 46 within breast 40, as described hereinabove.

The sensed signals from probe 92 are preferably normalized in any of the methods described above and the resulting images are preferably displayed to the physician on a screen (not shown). It is noted, however, that since the signals sensed by probe 92 are primarily from anomaly 46 it is possible to display the signals sensed by probe 92 after a primitive normalization or without any normalization for a partially degraded map.

Figure 7:
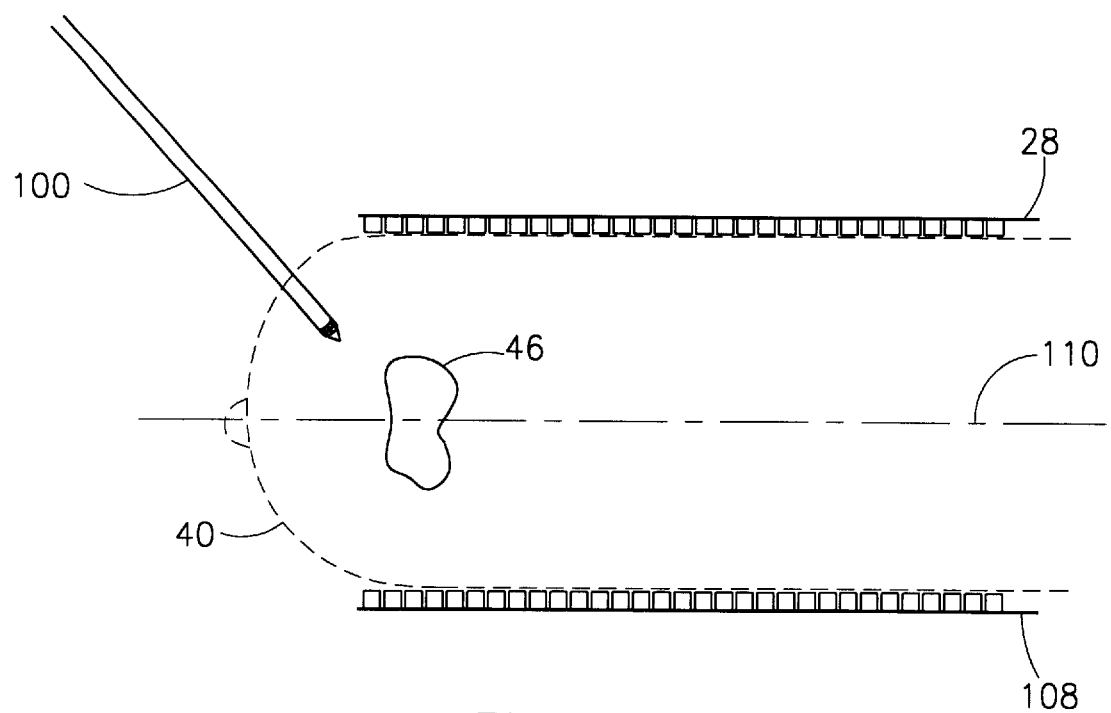
FIG. 7 is a schematic illustration of leading a needle, using impedance imaging control, in accordance with another preferred embodiment of the present invention.

FIG. 7 is a schematic illustration of a method of leading an impedance guided needle 100 toward a tumor 46 within a breast 40, in accordance with a preferred embodiment of the present invention. In the embodiment of FIG. 7, needle 100 generates electrifying signals so that the position of the needle relative to tumor 46 is easily viewed by a physician. Impedance guided needle 100 comprises a biopsy needle, or any other invasive tool, which is formed, at least partially, of a conducting material.

Electrical signals are preferably applied to needle 100 while it is inserted to breast 40. A probe 28 situated on an external side of breast 40 preferably senses the electrical signals reaching the surface of the breast. The signals from needle 100 appear on probe 28 in the form of a wedge-shaped line along the projection of the needle onto probe 28. The depth of needle 100 beneath probe 28 is related to the width of the wedge-shaped line, and in most practical applications can be assumed to be proportional to the width. This is because the farther needle 100 is from probe 28 the more the current from the needle disperses. In a preferred embodiment of the invention, a processor determines the width of the wedge-shaped line at the edges of needle 100 and accordingly determines the depth orientation of the needle within breast 40. The other orientations of needle 100 are determined from the projection of the needle on probe 28.

In addition to allowing the detection of the position and orientation of needle 100 within breast 40, currents from needle 100 preferentially flow through anomaly 46 because of the low impedance of the anomaly. As needle 100 approaches anomaly 46 the strength of the signals from anomaly 46 intensify, providing an additional indication of the location of the tip of needle 100 relative to anomaly 46. When needle 100 contacts anomaly 46, the tumor becomes substantially an electrical extension of needle 100, in a manner largely increasing the surface signals from anomaly 46, detected by probe 28.

In general, the signals applied to needle 100 induce a dipole within anomaly 46. The direction of the dipole within anomaly 46 depends on the relative orientation between needle 100 and anomaly 46. If needle 100 approaches anomaly 46 from the opposite side of probe 28, the dipole in anomaly 46 is directed toward probe 28 and is best detected by low input impedance sensors. If, on the other hand, needle 100 approaches anomaly 46 in an orientation perpendicular to probe 28, the dipole within the anomaly is perpendicular to probe 28. Therefore, the sensors on probe 28 are preferably given a high input impedance.

In a preferred embodiment of the present invention, in addition to electrifying needle 100, an external probe 108 applies signals to a surface of breast 40, preferably substantially opposite probe 28. Probe 108 is preferably similar to any of the embodiments of probe 30 described above although other probes may be used as well.

In a preferred embodiment of the present invention, probe 28 is held at an equipotential level and probe 108 applies voltage signals. The potential difference between probes 28 and 108 falls substantially equally over breast 40, since the impedance of the tissue of breast 40 is substantially constant. The electrifying signals applied to needle 100 are preferably voltage signals which are frequency and phase correlated with the signals from probe 108. Since needle 100 comprises a conducting material the signals applied to needle 100 are the same over the entire length of the needle. The voltage of breast 40 surrounding needle 100, on the other hand, depends on the distance of needle 100 from probes 108 and 28. In an example, based on DC voltages for simplicity, probe 28 is held at 0V and probe 108 is held at 2V. The central layer 110 between probes 28 and 108 is therefore at about 1V. If needle 100 is held at 1V, those parts of the needle which are above layer 110, closer to probe 28, are at voltage levels higher than their surrounding. Therefore, those parts of needle 100 give out currents to their surroundings, and appear on the screen as a line brighter than their surroundings. On the other hand, those parts of needle 100 which are below layer 110, closer to probe 108, appear on the screen darker than their surroundings.

In a preferred embodiment of the present invention, the voltage at which needle 100 is held is gradually changed until part of the needle appears darker than its surroundings and part of the needle appears lighter than its surroundings. At this state the voltage applied to needle 100 is equal to the voltage of the surroundings of the needle in at least one point. Based on this voltage, the depth of various portions of the needle within breast 40 can be estimated.

Alternatively or additionally, the voltage at which needle 100 is held is gradually changed until part of the needle disappears from the screen, joining the surroundings of the needle. This alternative is especially useful when needle 100 is substantially parallel to probe 28 and/or probe 108.

In a preferred embodiment of the invention, needle 100 and probe 108 apply signals of opposite polarity. Thus, a dipole is formed between needle 100 and surface probe 108, inducing a dipole within anomaly 46. When needle 100 forms contact with (or is very close to) anomaly 46, the polarity of the dipole reverses providing additional indication that needle 100 is in place.

Alternatively or additionally, the signals are applied to needle 100 and surface probe 108 at separate instances so that they do not interfere with each other. In a preferred embodiment of the present invention, signals are substantially constantly applied to surface probe 108 to receive a general map of a vicinity of needle 100. Periodically and/or when otherwise appropriate signals are applied to needle 100 in order to precisely determine the location of the needle.

Further alternatively or additionally, signals at one or more first frequencies are applied to surface probe 108 in order to detect the position of anomaly 46. Signals at one or more second frequencies are preferably applied to needle 100 so that it is possible to detect the position of the needle. In a preferred embodiment of the present invention, signals at one or more third frequencies are applied to both needle 100 and probe 108 in order to induce a dipole within anomaly 46 as described above. Preferably, the first, second and third frequencies are within a narrow band over which the impedance measure does not change significantly.

In a preferred embodiment of the present invention, at a first stage, signals are applied only to surface probe 108 in order to detect the location of anomaly 46 using any of the methods described above. These signals are preferably continuously applied in order to keep constant track of the detected anomaly 46. When needle 100 is directed to anomaly 46, signals are also applied to the needle to keep track of the movements of the needle and/or determine the relative position between the anomaly and the needle.

Figure 8:
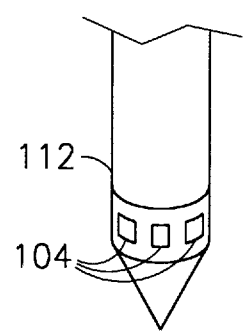
FIG. 8 is a schematic illustration of an invasive tool, in accordance with a preferred embodiment of the present invention.

FIG. 8 shows a biopsy needle 112, in accordance with a preferred embodiment of the invention, which is used to improve the accuracy of placement of the needle. Biopsy needle 112 includes a plurality of sensing elements 104 placed around the circumference of the needle, such that they indicate which portion of the needle is within a tumor to be biopsied. Alternatively or additionally, sensing elements 104 are spaced along the length of the needle. Leads (not shown) from each of these elements bring signals from the elements to a detection and computing system such as that described below. Alternatively, the electrodes may be circumferentially segmented (a lead being provided for each segment) so that information as to the direction of the tumor from the needle may be derived when the needle is not within the tumor.

Such an impedance sensing biopsy needle can be used, under guidance by palpation, ultrasound, x-ray mammography or other image from other image modalities (preferably including impedance imaging as described herein), taken during the biopsy or prior to the biopsy to improve the accuracy of placement of the needle. In particular, the impedance image from the needle may be combined with other images in a display. While this aspect of the invention has been described using a biopsy needle, this aspect of the invention is also applicable to positioning of any elongate object such as any other needle (such as a localizing needle), an endoscopic probe or a catheter.

In some preferred embodiments of the present invention, electrical signals are applied from probes 108 and/or 28 (FIG. 7) and the resultant signals are sensed by elements 104. In a preferred embodiment of the present invention, the readings on the different elements 104 are compared to determine which of elements 104 are in contact with anomaly 46. In a preferred embodiment of the invention, in which circumferentially segmented sensing elements are employed, the direction of the anomaly 46 relative to needle 112 is determined from the sensed signals. Alternatively or additionally, the sensed signals are used to determine the proximity of needle 112 to anomaly 46.

The image sensing biopsy needle can also be used with one or more imaging arrays (similar to those in probes 28 and 30) to impedance image the region to be biopsied during the biopsy procedure. Alternatively, at least one of the arrays can be an imaging array of the non-impedance type.

In some preferred embodiments of the present invention, one or more of the elements on the needle may themselves be electrified to cause them to "light up" on the image of probes 28 and/or 108. This electrification may be AC or DC may be the same or different from the primary image stimulus, may have a single frequency or a complex form and may be applied in a continuous or pulsed mode. In a preferred embodiment, elements 104 are electrified at various phases, for example at opposite polarities to provide electrification in the form of a dipole.

If one or more of the sensing elements is used in this manner for applying electrifying signals, the elements are preferably alternatively used to apply an electrification signal and to function as sensors, i.e., to sense signals from the primary stimulus.

In a preferred embodiment of the present invention, electrifying elements 104 face different directions of advancement. Preferably, when there is a doubt on the orientation of the needle, electrifying signals are applied sequentially to elements 104 and the orientation is determined accordingly, for example, according to the element 104 which induced the largest surface signals in probe 28.

It is noted that in a single biopsy procedure, elements 104 may serve both for applying electrical signals and for sensing signals. Alternatively or additionally, some of elements 104 serve as sensors and some apply signals, simultaneously.

In some preferred embodiments of the present invention, needle 112 includes, in addition to elements 104, a position sensor (not shown) of any kind known in the art which is used to locate the needle in a manner independent of the applied electrical signals. In a preferred embodiment of the present invention, the position sensor keeps track of the position of needle 112 even when electrical signals are not applied from elements 104. Preferably, after the position of needle 112 is determined relative to anomaly 46 using impedance imaging, the position of the needle in the impedance framework is registered with the position sensor framework, and the needle is tracked using the position sensor. Thus, it is possible to stop electrifying elements 104, for example in order not to interfere with precisely determining the position of anomaly 46.

It will be appreciated that the above described methods may be varied in many ways, including, changing the order of steps, and the exact implementation used. It should also be appreciated that the above described description of methods and apparatus are to be interpreted as including apparatus for carrying out the methods and methods of using the apparatus.

The present invention has been described using non-limiting detailed descriptions of preferred embodiments thereof that are provided by way of example and are not intended to limit the scope of the invention. It should be understood that features described with respect to one embodiment may be used with other embodiments and that not all embodiments of the invention have all of the features shown in a particular figure. Variations of embodiments described will readily occur to persons of the art. Furthermore, the terms "comprise," "include," "have" and their conjugates, shall mean, when used in the claims, "including but not necessarily limited to." The scope of the invention is limited only by the following claims:

What is claimed is:

1. A method of impedance imaging of a region within a body, comprising:
    positioning a multi-element probe, comprising a plurality of sensing elements, on one side of the region;
    positioning a plurality of electrifyable elements on a second side of the region;
    electrifying at least one of the plurality of electrifyable elements;
    measuring a signal at at least some of the sensing elements, the at least some of the sensing elements including more elements than the number of electrified elements; and
    analyzing the region responsive to the measured signals and the positions of the electrified elements.

2. A method according to claim 1, wherein the electrified elements cover an area which is less than ten percent of a face area of the multi-element probe.

3. A method according to claim 1, wherein positioning the electrifyable elements comprises mounting the electrifyable elements on an invasive tool inserted into the region.

4. A method according to claim 1, wherein electrifying the electrifyable elements comprises applying at least two electrifying signals with different phases.

5. A method according to claim 4, wherein applying the at least two electrifying signals comprises applying signals of substantially opposite polarity.

6. A method according to claim 1, wherein positioning the multi-element probe comprises holding substantially all of the sensing elements of the multi-element probe at a same potential.

7. A method according to claim 1, wherein positioning the multi-element probe comprises positioning a probe of which a plurality of the sensing elements are simultaneously connected to respective sensors and wherein measuring the signal at at least some of the elements comprises measuring at less than all the plurality of sensing elements which are simultaneously connected.

8. A method according to claim 7, wherein measuring comprises measuring using less than ten percent of the sensing elements at any single time.

9. A method according to claim 1, wherein at least some of the sensing elements have a low input impedance.

10. A method according to claim 1, wherein at least some of the sensing elements have a high input impedance.

11. A method according to claim 1, wherein positioning the electrifyable elements on the second side of the region comprises positioning the elements on a side of the region substantially opposite the multi-element probe.

12. A method according to claim 1, wherein analyzing the region comprises producing an impedance map responsive to the measured signals.

13. A method according to claim 12, wherein producing the impedance map comprises normalizing the impedance map responsive to the positions of the electrified elements.

14. A method according to claim 13, wherein normalizing the impedance map comprises subtracting a predetermined background map from the produced map.

15. A method according to claim 13, wherein normalizing the impedance map comprises subtracting, from values of the measured signals of at least one group of sensing elements, a representative value which is a function of the measured values of the at least one group.

16. A method according to claim 15, wherein the representative value of the at least one group comprises an average of the measured values of the at least one group.

17. A method according to claim 15, wherein the representative value of the at least one group comprises a minimum of the measured values of the at least one group.

18. A method according to claim 1, wherein the electrified elements form a long and narrow straight line of elements.

19. Method according to claim 1, wherein analyzing the region comprises determining whether a suspected lesion exists in the region.

20. A method according to claim 1, wherein analyzing the region comprises determining a location of a lesion within the region.

21. A method according to claim 20, wherein determining the location of the lesion comprises determining a depth of the lesion below the multi-element probe.

22. A method according to claim 21, wherein determining the depth of the lesion comprises generating a map of sensed signals responsive to the signals measured by the at least some sensing elements of the multi-element probe and determining the depth responsive to a distance between peaks in the generated map.

23. A method according to claim 1, wherein positioning the electrifyable elements comprises positioning a second multi-element probe comprising the electrifyable elements.

24. A method according to claim 23, comprising sequentially electrifying and measuring while electrifying different sub-groups of elements of the second multi-element probe.

25. A method according to claim 24, wherein sequentially electrifying comprises sequentially electrifying columns of the second multi-element probe.

26. A method according to claim 24, wherein sequentially electrifying comprises sequentially electrifying pairs of one-dimensional strips of the second multi-element probe.

27. A method according to claim 26, wherein sequentially electrifying the pairs of one-dimensional strips comprises electrifying the one-dimensional strips with signals of respective opposite polarities.

28. A method according to claim 26, wherein electrifying the pairs of one-dimensional strips comprises electrifying pairs of one-dimensional strips which are separated by a predetermined distance, to form a dipole source of electrification.

29. A method of impedance imaging of a region, comprising:
    positioning a multi-element probe, comprising a plurality of sensing elements, on one side of the region;
    providing electrifying signals to the region from one or more first locations;
    measuring a signal at at least some of the elements of the multi-element probe responsive to the signals from the one or more first locations;

providing electrifying signals to the region from one or more second locations different from the first locations;

measuring a signal at at least some of the elements of the multi-element probe responsive to the signals from the one or more second locations;

generating first and second maps of the region responsive to the signals measured responsive to the electrifying signals of the first and second locations, respectively; and analyzing the region responsive to the first and second maps.

30. A method according to claim 29, wherein providing the electrifying signals from the one or more first and second locations comprises providing electrifying signals to a second multi-element probe.

31. A method according to claim 29, wherein measuring the signal at at least some of the elements comprises measuring at substantially all the elements of the multi-element probe.

32. A method according to claim 29, wherein analyzing the region comprises analyzing responsive to the measurements and the one or more first and second locations.

33. A method of impedance imaging of a region, comprising:

positioning a multi-element probe, comprising a plurality of sensing elements, on a surface of the region;

providing an electrifying field to the region substantially in the form of a dipole; and measuring a signal at at least some of the elements of the multi-element probe responsive to the electrifying field.

34. A method according to claim 33, wherein providing the dipole electrifying field comprises providing signals of opposite polarity to spaced electrifyable elements.

35. A method according to claim 33, wherein providing the electrifying field comprises providing the field from a dipole formed of parallel lines.

36. A method of impedance imaging of a region, comprising:

positioning a multi-element probe, comprising a plurality of sensing elements, having low input impedance, on a surface of the region;

providing a plurality of electrifying fields having a common frequency, different amplitudes and different phases to the region; and measuring an electrical current signal at at least some of the elements of the multi-element probe responsive to the electrifying fields.

37. A method according to claim 36, wherein providing the plurality of electrifying fields comprises providing fields which comprise a dipole field.

38. A method according to claim 36, wherein providing the plurality of electrifying signals comprises providing signals which have voltages such that the sum of the voltages of the signals is substantially zero at substantially any time.

39. A method of impedance imaging of a region, comprising:

positioning a multi-element probe, comprising a plurality of sensing elements, on a surface of the region;

applying an electrical field to the region;

connecting at least some of the sensing elements of the multi-element probe to a sensor through a high input impedance;

measuring an electrical signal produced by at least some of the sensing elements with the high input impedance sensor; and generating a multi-pixel map of the region in which each pixel has a value that depends on measurements from up to two sensing elements.

40. A method according to claim 39, wherein applying the electrical field comprises applying signals to a pair of electrodes on substantially opposite sides of the region.

41. A method according to claim 40, wherein applying the signals to the pair of electrodes comprises applying signals to a pair of electrodes positioned such that a straight line connecting the electrodes is substantially parallel to the multi-element probe.

42. A method according to claim 41, wherein applying the signals to the pair of electrodes comprises applying signals to a pair of electrodes positioned substantially perpendicular to the multi-element probe.

43. A method according to claim 41, wherein applying the signals to the pair of electrodes comprises applying signals to a pair of electrodes such that the combined field produced by electrification of the pair of electrodes is substantially parallel to the multi-element probe.

44. A method according to claim 40, wherein applying the signals comprises applying signals of a different amplitude to each of the electrodes.

45. A method according to claim 44, wherein applying the signals to the pair of electrodes comprises holding one of the electrodes at a ground potential.

46. A method of impedance imaging of a region, comprising:

positioning a multi-element probe, comprising a plurality of sensing elements, on a surface of the region;

positioning a pair of electrodes on substantially opposite sides of the region;

electrifying the pair of electrodes to provide an electrical field between the pair of electrodes;

measuring an electrical signal by pairs of the sensing elements responsive to the electrifying of the pair of electrodes; and generating a multi-pixel map of the region in which each pixel has a value which depends on measurements from up to two sensing elements.

47. A method according to claim 46, wherein producing the impedance map comprises producing the map responsive to the difference between the signals measured by at least two adjacent sensing elements.

48. A method of determining the position of an anomaly within a region of a body, comprising:

applying electrifying signals to the region;

determining a response map along a surface of the region responsive to the applied signals;

determining a point on the surface which is above the anomaly responsive to the response map; and calculating a depth from the determined point to the anomaly responsive to the response map.

49. A method according to claim 48, wherein determining the response map comprises determining a map which covers less than half the total surface area of the region.

50. A method according to claim 48, wherein determining the response map comprises determining a plurality of maps generated responsive to different patterns of electrifying signals.

51. A method according to claim 48, wherein determining the point above the anomaly comprises finding a point located between a pair of peaks on the map.

52. A method according to claim 51, wherein calculating the depth comprises determining a distance between the pair of peaks.

53. A method according to claim 48, wherein applying electrifying signals to the region comprises inducing a dipole which is substantially parallel to the surface along which the response map is determined.

54. A method of guiding an elongate object within a region of a subject, comprising:
providing electrifying signals to at least a part of the elongate object within the region;
measuring electrical signals on a surface of the region;
moving the elongate object;
comparing the electrical signals measured on the surface of the region before and after the movement; and
determining desired movements of the object responsive to the comparison.

55. A method according to claim 54, wherein the elongate object comprises a biopsy needle.

56. A method according to claim 54, wherein providing the electrifying signals comprises providing the signals to a probe mounted on the elongate object.

57. A method according to claim 54, wherein providing the electrifying signals comprises electrifying the elongate object.

58. A method according to claim 54, wherein determining the desired movements comprises determining a movement direction which enhances the measured signals.

59. A method according to claim 54, and further comprising providing electrifying signals from a surface of the region.

60. A method according to claim 59, wherein providing the electrifying signals from the surface comprises providing signals different from the signals provided to the at least part of the elongate object.

61. A method according to claim 60, wherein providing the electrifying signals from the surface comprises providing signals of opposite polarity of the signals provided to the elongate object.

62. A method for determining the location of an elongate object in a region of a subject, comprising:
providing electrifying signals to at least a part of the elongate object within the region;
measuring electrical signals on a surface of the region; and
determining the location of the object responsive to the measured electrical signals.

63. A method according to claim 62, wherein determining the location comprises determining when the object is touching an anomaly.

64. A method according to claim 63, wherein determining when the object is touching the anomaly comprises determining reversal of the polarity of the measured signals.

65. A method according to claim 62, wherein providing the electrifying signals comprises electrifying the elongate object.

66. A method according to claim 62, wherein determining the location of the object comprises determining a depth of a plurality of points along the elongate object.

67. A method according to claim 62, wherein measuring the electrical signals comprises producing a two dimensional map of signals on the surface of the region.

68. A method according to claim 67, wherein determining the location of the object comprises determining a depth of the object responsive to the width of an image of the object on the two dimensional map.

69. A method according to claim 67, wherein determining the location of the object comprises determining a depth of the object responsive to the strength of the signals on the two dimensional map.

70. A method according to claim 62, and further comprising providing electrifying signals to the region from a surface of the region.

71. A method according to claim 70, comprising varying the amplitude of the signals provided to the at least part of the elongate object.

72. A method according to claim 71, wherein determining the location of the object comprises generating a two dimensional map responsive to the measured signals and determining an amplitude of the electrifying signals provided to the object at which at least part of an image of the object on the map is not distinguishable from its surroundings.

73. A method according to claim 71, wherein determining the location of the object comprises generating a two dimensional map responsive to the measured signals and determining an amplitude of the electrifying signals provided to the object at which at least part of an image of the object is darker than its surroundings on the map and at least part of the image of the object is brighter than its surroundings on the map.

74. A method for determining a location of an elongate object in a region of a subject, comprising:
providing electrifying signals to a part of the elongate object within the region;
measuring electrical signals on a surface of the region;
generating a map of the region responsive to the measured signals; and
changing the electrical signals provided to the elongate object so that the surface signals generated responsive to the signals provided to the elongate object are lower than surrounding surface signals on the map at a first portion of the map and higher than surrounding surface signals on the map at a second portion of the map.

75. A method according to claim 74, wherein changing the electrical signals comprises changing an amplitude of the signals.

76. A method according to claim 74, wherein determining the location of the object comprises determining a depth of the object responsive to the amplitude of the changed signals.

77. A method of guiding an elongate object within a region of a subject, comprising:
providing electrifying signals to the region;
measuring electrical signals incident on the elongate object within the region; and
determining desired movements of the object responsive to the measured signals.

78. A method according to claim 77, wherein providing electrifying signals comprises providing signals from a surface of the region.

79. Apparatus for impedance imaging of a region within a body, comprising:
a first multi-element probe, comprising a plurality of sensing elements, for positioning on one side of the region;
a second multi-element probe for positioning on a second side of the region and for generating signals to be sensed by the first multi-element probe; and
a controller which electrifies a first set of fewer than all of the elements of the second multi-element probe and a second set, different from the first set, of the elements of the second multi-element probe, and analyzes the region responsive to the electrification of the first and second sets of elements,
wherein the first and second sets of elements are electrified at non-concurrent times.

80. Apparatus according to claim 79, wherein the controller initiates measuring of a signal at less than all of the elements of the first multi-element probe.

81. Apparatus according to claim 79, wherein the controller electrifies fewer than ten percent of the elements of the second multi-element probe concurrently.

82. Apparatus according to claim 79, wherein the controller applies concurrently to different ones of at least some of the elements, at least two electrifying signals with different phases.

83. Apparatus according to claim 79, wherein the controller applies concurrently to at least some of the elements, at least two electrifying signals with substantially opposite polarity.

84. Apparatus according to claim 79, wherein at least some of the elements of the first multi-element probe are allowed to float electrically.

85. Apparatus according to claim 79, wherein at least some of the elements of the first multi-element probe are held at an equipotential level.

86. Apparatus according to claim 79, wherein the elements of the second multi-element probe comprise long and narrow straight elements.

87. Apparatus according to claim 79, wherein the controller sequentially electrifies different groups of the elements of the second multi-element probe.

88. Apparatus according to claim 87, wherein the sequentially electrified groups form long and narrow patterns.

89. Apparatus according to claim 79, wherein the probes are cup-shaped.

90. Apparatus according to claim 79, wherein the first probe comprises a rectangular probe.

91. Apparatus according to claim 79, wherein the plurality of sensing elements have low input impedance.

92. Apparatus for impedance imaging of a region, comprising:
a first, multi-element, probe, comprising a plurality of sensing elements, for positioning on one side of the region; and
a second probe which applies electrifying signals which form a dipole, to the region.

93. Apparatus according to claim 92, wherein the second probe comprises two groups of elements of substantially equal extent which provide signals of opposite polarity.

94. Apparatus for impedance imaging of a region, comprising:
an electrifying probe which applies a plurality of distinct electrifying signals to the region;
a sensing probe, comprising a two dimensional array of sensing elements which sense signals generated responsive to the plurality of distinct electrifying signals; and
an image generator adapted to generate a multi-pixel map of the region including a pixel value for substantially each sensing element of the sensing probe.

95. Apparatus according to claim 94, wherein the plurality of distinct electrifying signals are of substantially the same frequency.

96. Apparatus according to claim 94, wherein the plurality of distinct electrifying signals are of substantially the same amplitude.

97. Apparatus according to claim 94, wherein the plurality of distinct electrifying signals have different phases.

98. Apparatus for impedance imaging of a region of a subject, comprising:
a plurality of electrodes for applying, substantially concurrently, electrifying signals having a common frequency and different amplitudes to the subject; and
a probe comprising a plurality of sensing elements, having low input impedance, for sensing electrical current signals induced by the applied signals.

99. Apparatus according to claim 98, wherein the plurality of electrodes comprise at least one first electrode which applies currents to the region and at least one second electrode which attracts currents from the region.

100. Apparatus according to claim 99, wherein the at least one second electrode and the at least one first electrode are adapted to be positioned on opposite sides of the region.

101. Apparatus according to claim 98, wherein the probe comprises at least one sensing element having a high input impedance.

102. Apparatus according to claim 101, wherein the probe comprises at least one sensing element having a low input impedance.

103. Apparatus according to claim 98, wherein the probe comprises at least one sensing element having a controllable input impedance.

104. Apparatus according to claim 98, wherein the plurality of electrodes are included in an electrode probe different from the probe including a plurality of sensing elements.

105. Apparatus for sensing electrical signals from a tissue surface, comprising:
at least one contact surface suitable for contact with the tissue surface; and
a sensing circuit with a controllable input impedance, adapted to sense electrical signals incident on the at least one contact surface, with a plurality of different input impedance values.

106. Apparatus according to claim 105, wherein the sensing circuit comprises one or more switches which select one of a plurality of predetermined input impedance values.

107. Apparatus for impedance imaging of a region within a body, comprising:
a probe comprising a two-dimensional rectangular array of electrifyable elements capable of electrifying the region;
a multi-element probe, comprising a plurality of sensing elements, capable of measuring signals from the region; and
circuitry which electrifies a group including at least one column or row of the electrifyable elements, and is capable of determining at least one characteristic of an anomaly in the region responsive to signals measured by at least some of the sensing elements responsive to the electrification of the group of electrifyable elements.

108. Apparatus according to claim 107, wherein the circuitry comprises dedicated hardware.

109. Apparatus according to claim 107, wherein the circuitry comprises a general purpose processor and compatible software.

110. Apparatus according to claim 107, wherein the probe comprising the electrifyable elements is mounted on an invasive tool inserted into the region.

111. Apparatus according to claim 107, wherein the multi-element probe is mounted on an invasive tool inserted into the region.

112. Apparatus according to claim 107, wherein the circuitry generates a current tracing map responsive to the measured signals.

113. Apparatus according to claim 112, wherein the circuitry normalizes the current tracing map.

114. Apparatus according to claim 113, wherein the circuitry normalizes the map by subtracting background values from the generated map.

115. Apparatus according to claim 113, wherein the circuitry normalizes the map by subtracting, from the measured signals of at least one group of elements, a representative value of the group.

116. Apparatus according to claim 107, wherein the circuitry is capable of determining whether an anomaly exits in the region.

117. Apparatus according to claim 107, wherein the circuitry is capable of determining a position of the anomaly in the region.

118. Apparatus according to claim 107, wherein the circuitry is capable of determining a medical diagnosis of the anomaly.

119. Apparatus according to claim 107, wherein the circuitry sequentially electrifies a plurality of rows or lines of the two-dimensional array.

120. Apparatus according to claim 107, wherein the circuitry electrifies concurrently at least two rows or lines of the two-dimensional array.

121. Apparatus according to claim 120, wherein the circuitry electrifies concurrently at least two rows or lines of the two-dimensional array with signals having different amplitudes, frequencies or phases.

122. A method of impedance imaging of a region, comprising:

positioning a probe, comprising a plurality of sensing elements, on a surface of the region;

simultaneously applying electrifying signals at a plurality of distinct frequencies to the region through different electrifying elements; and measuring electrical signals by at least some of the sensing elements responsive to the applied electrifying signals; and generating separate maps for a plurality of the distinct frequencies responsive to the measured electrical signals.

123. A method according to claim 122, wherein measuring the electrical signals comprises sampling signals adjacent the sensing elements a predetermined number of times and wherein the number of distinct frequencies comprises substantially the maximal number allowed by the predetermined number of samplings according to Nyquist's law.

124. A method according to claim 122, comprising selecting a plurality of beginning frequencies and adjusting the frequencies so as to fit into nearest vacant Nyquist bins in order to receive the distinct frequencies.

125. A method according to claim 124, wherein selecting the plurality of beginning frequencies comprises selecting based on physiological characteristics of the region.

126. A method according to claim 125, wherein adjusting the frequencies comprises adjusting low frequencies before high frequencies.

127. A method according to claim 122, wherein applying electrifying signals at a plurality of distinct frequencies comprises applying signals at frequencies only within a narrow band in which impedance measures do not change substantially.

128. A method according to claim 127, wherein the narrow band is narrower than 1000 Hz.

129. A method according to claim 122, wherein generating the separate maps is performed using a single FFT operation.

130. A method according to claim 129, wherein the distinct frequencies are selected so as to allow generating the separate maps using the single FFT operation.

131. A method of impedance imaging of a region, comprising:

positioning a multi-element probe, comprising a plurality of sensing elements, on a surface of the region;

providing a plurality of electrifying fields of different phases to the region, from one or more electrodes separate from the multi-element probe;

measuring a signal at at least some of the elements of the multi-element probe responsive to the electrifying fields; and generating a multi-pixel map having a respective pixel value for each of the sensing elements.

* * * * *